(12) United States Patent
Woodbury et al.

(10) Patent No.: US 10,046,293 B2
(45) Date of Patent: Aug. 14, 2018

(54) IN SITU CHEMICAL PATTERNING

(71) Applicant: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

(72) Inventors: Neal Woodbury, Tempe, AZ (US); Stephen Albert Johnston, Tempe, AZ (US)

(73) Assignee: ARIZONA BOARD OF REGENTS, A BODY CORPORATE OF THE STATE OF ARIZONA, Scottsdale, AZ (US)

( * ) Notice: Subject to any disclaimer, the term of this patent is extended or adjusted under 35 U.S.C. 154(b) by 264 days.

(21) Appl. No.: 14/436,465

(22) PCT Filed: Oct. 17, 2013

(86) PCT No.: PCT/US2013/065541
§ 371 (c)(1),
(2) Date: Apr. 16, 2015

(87) PCT Pub. No.: WO2014/062981
PCT Pub. Date: Apr. 24, 2014

(65) Prior Publication Data
US 2015/0217258 A1 Aug. 6, 2015

Related U.S. Application Data
(60) Provisional application No. 61/715,201, filed on Oct. 17, 2012.

(51) Int. Cl.
*B01J 19/00* (2006.01)
*C07K 1/04* (2006.01)

(52) U.S. Cl.
CPC ........... *B01J 19/0046* (2013.01); *C07K 1/047* (2013.01); *B01J 2219/00596* (2013.01); *B01J 2219/00722* (2013.01); *B01J 2219/00725* (2013.01)

(58) Field of Classification Search
None
See application file for complete search history.

(56) References Cited

U.S. PATENT DOCUMENTS

| 5,384,261 | A | | 1/1995 | Winkler et al. |
|---|---|---|---|---|
| 5,424,186 | A | | 6/1995 | Fodor et al. |
| 5,565,332 | A | * | 10/1996 | Hoogenboom ........ C07K 16/18 435/235.1 |
| 5,571,639 | A | | 11/1996 | Hubbell et al. |
| 6,083,697 | A | | 7/2000 | Beecher et al. |
| 6,153,743 | A | | 11/2000 | Hubbell et al. |
| 2003/0050438 | A1 | | 3/2003 | Montgomery |
| 2004/0038556 | A1 | | 2/2004 | French et al. |
| 2004/0063902 | A1 | | 4/2004 | Miranda |
| 2005/0156499 | A1 | | 7/2005 | Dinu et al. |
| 2007/0122841 | A1 | | 5/2007 | Rajasekaran et al. |
| 2007/0122842 | A1 | | 5/2007 | Rajasekaran et al. |
| 2008/0124719 | A1 | | 5/2008 | Chung et al. |
| 2009/0258796 | A1 | | 10/2009 | Rajasekaran et al. |
| 2010/0261205 | A1 | | 10/2010 | Kakuta et al. |
| 2011/0105366 | A1 | | 5/2011 | Lebl et al. |
| 2014/0087963 | A1 | * | 3/2014 | Johnston ............ G01N 33/6893 506/9 |
| 2015/0141296 | A1 | | 5/2015 | Woodbury et al. |

FOREIGN PATENT DOCUMENTS

| WO | WO-9727329 A1 | 7/1997 |
|---|---|---|
| WO | WO-2008151146 A2 | 12/2008 |
| WO | WO-2013063133 A1 | 5/2013 |
| WO | WO2014036312 * | 3/2014 |
| WO | WO-2014062981 A1 | 4/2014 |

OTHER PUBLICATIONS

Japanese Application No. 2012-516358 Office Action dated Jun. 16, 2015.
U.S. Appl. No. 13/379,080 Final Office Action dated Jul. 21, 2015.
Boltz, et al. Peptide microarrays for carbohydrate recognition. Analyst. Apr. 2009;134(4):650-2. doi: 10.1039/b823156g. Epub Feb. 11, 2009.
Fodor et al., Light-directed, spatially addressable parallel chemical synthesis, Science, Feb. 1991, 767-73, vol. 251, No. 4995.
Fu et al., Exploring peptide space for enzyme modulators, J. Am. Chem. Soc., Apr. 2010, 6419-6424, vol. 132, No. 18.
Fu et al., Interenzyme substrate diffusion for an enzyme cascade organized on spatially addressable DNA nanostructures, J Am Chem Soc., Mar. 2012, 5516-9, vol. 134, No. 12.
Fu, et al. Peptide-modified surfaces for enzyme immobilization. PLoS One. Apr. 8, 2011;6(4):e18692. doi: 10.1371/journal.pone.0018692.
Greving et al., Feature-level MALDI-MS characterization of in situ-synthesized peptide microarrays, Langmuir, Feb. 2009, 1456-1459, vol. 26, No. 3.
Gupta, N., et al. Engineering a synthetic ligand for tumor necrosis factor-alpha.(2011) Bioconjugate Chemistry, vol. 22, pp. 1473-1478.
Han et al., DNA origami with complex curvatures in three-dimensional space, Science, Apr. 2011, 342-346, vol. 332, No. 6027.
Hughes, et al. Immunosignaturing can detect products from molecular markers in brain cancer. PLoS One. 2012;7(7):e40201. doi: 10.1371/journal.pone.0040201. Epub Jul. 16, 2012.
International search report and written opinion dated Oct. 22, 2012 for PCT/US2012/036631.
International search report dated Dec. 20, 2013 for PCT/US2013/065541.

(Continued)

*Primary Examiner* — Christopher M Gross
(74) *Attorney, Agent, or Firm* — Wilson Sonsini Goodrich & Rosati

(57) ABSTRACT

Provided herein are methods and devices for performing in situ patterned chemistry for synthesizing and preparing peptide arrays. The invention provides a reproducible and scalable platform that can be potentially used to monitor the health of a plurality of individuals.

19 Claims, 22 Drawing Sheets

(56) References Cited

OTHER PUBLICATIONS

Ke et al., Self-assembled water-soluble nucleic acid probe tiles for label-free RNA hybridization assays, Science, Jan. 2008, 180-183, vol. 319, No. 5860.

Legutki, et al. A general method for characterization of humoral immunity induced by a vaccine or infection. Vaccine. Jun. 17, 2010;28(28):4529-37. doi: 10.1016/j.vaccine.2010.04.061. Epub May 5, 2010.

Lund, et al., Molecular robots guided by prescriptive landscapes, Nature, May 2010, 206-210, vol. 465, No. 7295.

Moller, et al. DNA probes on chip surfaces studied by scanning force microscopy using specific binding of colloidal gold. Nucleic Acids Res. Oct. 15, 2000;28(20):E91.

Northen et al., Combinatorial screening of biomimetic protein affinity materials, Adv Mater., Oct. 2008, 4691-4697, vol. 20, No. 24.

Price et al., On silico peptide microarrays for high-resolution mapping of antibody epitopes and diverse protein-protein interactions, Nat Med, Sep. 2012, 1434-40, vol. 18, No. 9.

Restrepo, et al. Application of immunosignatures to the assessment of Alzheimer's disease. Ann Neurol. Aug. 2011;70(2):286-95. doi: 10.1002/ana.22405.

Shan et al., Imaging local electrochemical current via surface plasmon resonance, Science, Mar. 2010, 1363-66, vol. 327, No. 5871.

Sharma et al., Control of self-assembly of DNA tubules through integration of gold nanoparticles, Science, Jan. 2009, 112-116, vol. 323, No. 5910.

Singh-Gasson et al., Maskless fabrication of light-directed oligonucleotide microarrays using a digital micromirror array, Nat Biotechnol, Oct. 1999, 974-978, vol. 17, No. 10.

Takulapalli et al., Electrical detection of amine ligation to a metalloporphyrin via a hybrid SOI-MOSFET, J. Am. Chem. Soc., Jan. 2008, 2226-2233, vol. 130, No. 7.

Wilk et al., Integrated electrodes on a silicon based ion channel measurement platform, Biosensors and Bioelectronics, Sep. 2007, 183-190, vol. 23, No. 2.

Williams et al., Creating protein affinity reagents by combining peptide ligands on synthetic DNA scaffolds, J. Am Chem Soc., Dec. 2009, 17233-17241, vol. 131, No. 47.

Zhang et al., Reversible oxygen gas sensor based on electrochemiluminescence., Chemical Communications, May 2010, 3333-3335, vol. 46, No. 19.

U.S. Appl. No. 14/116,749 Non-Final Office Action dated Sep. 20, 2017.

U.S. Appl. No. 14/116,749 Restriction Requirement dated Apr. 26, 2017.

* cited by examiner

FIGURE 18

Trp    S-Trp

IN SITU CHEMICAL PATTERNING

CROSS-REFERENCE

This application claims the benefit of U.S. Provisional Application No. 61/715,201 filed on Oct. 17, 2012, entitled "In Situ Chemical Patterning," which is incorporated herein by reference in its entirety.

GOVERNMENT SPONSORED WORK

This invention was made with government support under HDTRAA-12-C-0058 awarded by DTRA (Defense Threat Reduction Agency). The government has certain rights to this invention.

BACKGROUND OF THE INVENTION

The present invention provides for methods and devices for generating a minimum number of patterning steps for synthesizing and preparing chemical libraries.

SUMMARY OF THE INVENTION

Provided herein are methods and devices for performing in situ patterned chemistry for synthesizing and preparing chemical libraries.

Disclosed herein are in situ synthesized randomized chemical libraries, wherein the synthesis of the chemical libraries uses a minimum number of patterning steps to construct the library, comprising:
 a) determining a minimum number of patterned steps to synthesize the chemical library;
 b) assigning an activated or inactivated designation to each feature;
 c) assigning a monomer to each feature that is designated as activated; and
 d) coupling the monomers on the substrate at each feature that is designated as activated; wherein the monomers are sequentially coupled for the minimum number of patterned steps of a).

In some embodiments, the invention provides an in situ synthesized chemical library, wherein said synthesis uses a minimum number of patterned steps to construct the library, comprising:
 a) determining a minimum number of patterns in a pattern set to synthesize the randomized chemical library, wherein the number of patterns in a pattern set is less than the number of patterns needed to synthesize a unique set of sequences;
 b) assigning to each feature on a pattern a clear (activated) or opaque (closed) designation;
 c) assigning a monomer to each pattern comprising a clear (activated) or opaque (closed) designation at each feature; and
 d) coupling monomers on the substrate at each clear (activated) designation on each pattern;
 wherein the monomers are sequentially coupled for each pattern in the pattern set.

In some embodiments, the minimum number of patterns in a pattern set is at least 33% of the number of patterned steps needed to construct an uncorrelated set of sequences in the chemical library.

In some embodiments, synthesis of the chemical libraries is photolithography-based. In some embodiments, the photolithography-based synthesis comprises a photomask patterned step.

In some embodiments, each feature on the photomask is randomly assigned an activated or inactivated designation.

In other embodiments, the photolithography-based synthesis of the chemical libraries uses a minimum number of photomasks to construct the chemical library. In some embodiments, the photomasking step photomasks a feature of about 0.5 micron to about 200 microns in diameter and a center-to-center distance of about 1 micron to about 300 microns on center.

In some embodiments, the number of photomasks needed to construct the chemical library is about 33% to about 95% of the number of masks needed to construct a random chemical library. In other embodiments, the number of photomasks needed to construct the chemical library is about 51% to about 75% of the number of masks needed to construct a random chemical library. In yet other embodiments, the number of photomasks needed to construct the chemical library is about 51% to about 55% of the number of masks needed to construct a random chemical library.

In some embodiments, the library comprises at least 10,000 features on the substrate. In some embodiments, the library comprises at least 100,000 features on the substrate. In other embodiments, the library comprises at least 330,000 features on the substrate. In some embodiments, the library comprises at least 1,000,000 features on the substrate. In some embodiments, the library comprises at least 100,000,000 features on the substrate. In some embodiments, the substrate is selected from the group consisting of arrays, wafers, slides, and beads.

In some embodiments, the synthesized chemical structures are peptides or nucleotides. In other embodiments, the peptides are about 5 amino acids in length to about 25 amino acids in length. In some embodiments, the amino acids C, I, T and M, and optionally Q and E, are not included in the amino acids available for peptide synthesis. In yet other embodiments, the lengths of peptides between each feature is not uniform.

Also disclosed herein are methods of in situ synthesizing a chemical library on a substrate, wherein the number of patterning steps needed to construct the library are minimized, the method comprising:
 a) determining a minimum number of patterned steps to synthesize the chemical library, wherein the minimum number of patterns in a pattern set is at least 33% of the number of patterned steps needed to construct an uncorrelated set of sequences in the chemical library and the total number of patterned steps determines a degree of randomness of the chemical library;
 b) assigning an activated or inactivated designation to each feature;
 c) assigning a monomer to each feature that is designated as activated; and
 d) coupling the monomers on the substrate at each feature that is designated as activated; wherein the monomers are sequentially coupled for the minimum number of patterned steps of a).

In some embodiments, the invention provides a methods for in situ synthesizing chemical libraries on a substrate, wherein the number of patterning steps needed to construct the library are minimized, the method comprising:
 a) determining a minimum number of patterns in a pattern set to synthesize the randomized or pseudo-randomized chemical library, wherein the minimum number of patterns in a pattern set is at least 33% of the number of patterned steps needed to construct an uncorrelated set of sequences in the chemical library and the number of patterns in a pattern set is less than the number of patterns needed to synthesize a unique set of sequences;

b) assigning to each feature on a pattern a clear (activated) or opaque (closed) designation;

c) assigning a monomer to each pattern comprising a clear (activated) or opaque (closed) designation at each feature;

d) coupling monomers on the substrate at each clear (activated) designation on each pattern;

wherein the monomers are sequentially coupled for each pattern in the pattern set.

In some embodiments, a method for in situ synthesis of the chemical libraries is photolithography-based. In some embodiments, the photolithography-based synthesis comprises a photomask patterned step.

In some embodiments, a method for the photolithography-based synthesis of the chemical libraries uses a minimum number of photomasks to construct the chemical library. In some embodiments, the photomasks comprise a feature of about 0.5 micron to about 200 microns in diameter and a center-to-center distance of about 1 micron to about 300 microns on center.

In some embodiments, the synthesis is photolithography based. In some embodiments, the said photolithography-based synthesis uses a minimum number of photopatterns to construct the chemical library. In some embodiments, the number of photomasks needed to construct the chemical library is about 33% to about 95% of the number of masks needed to construct a random chemical library. In other embodiments, the number of photomasks needed to construct the chemical library is about 51% to about 75% of the number of masks needed to construct a random chemical library. In yet other embodiments, the number of photomasks needed to construct the chemical library is about 51% to about 55% of the number of masks needed to construct a random chemical library.

In some embodiments, the library comprises at least 100,000 features on the substrate. In other embodiments, the library comprises at least 330,000 features on the substrate. In still other embodiments, the library comprises at least 1,000,000 features on the substrate. In yet other embodiments, the library comprises at least 100,000,000 features on the substrate. In some embodiments, the substrate is selected from the group consisting of arrays, wafers, slides, and beads.

In some embodiments, the synthesized chemical structures are peptides or nucleotides. In other embodiments, the peptides are about 5 amino acids in length to about 25 amino acids in length. In some embodiments, the amino acids C, I, T, and M, and optionally Q and E, are not included in the amino acids available for peptide synthesis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 18:
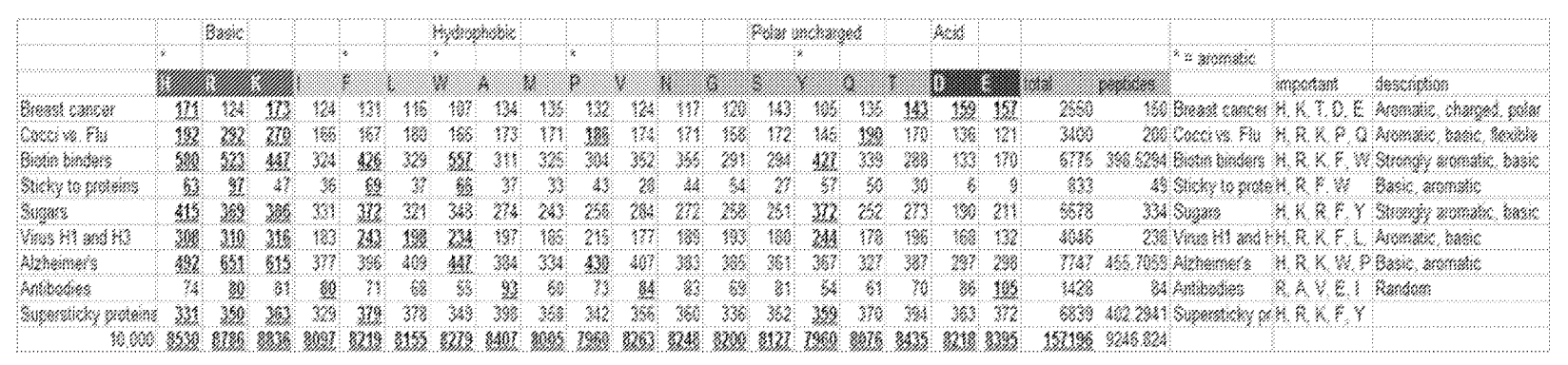

FIG. 18 depicts the contribution of individual amino acids in immunosignature arrays.

DETAILED DESCRIPTION OF THE INVENTION

Figure 1:
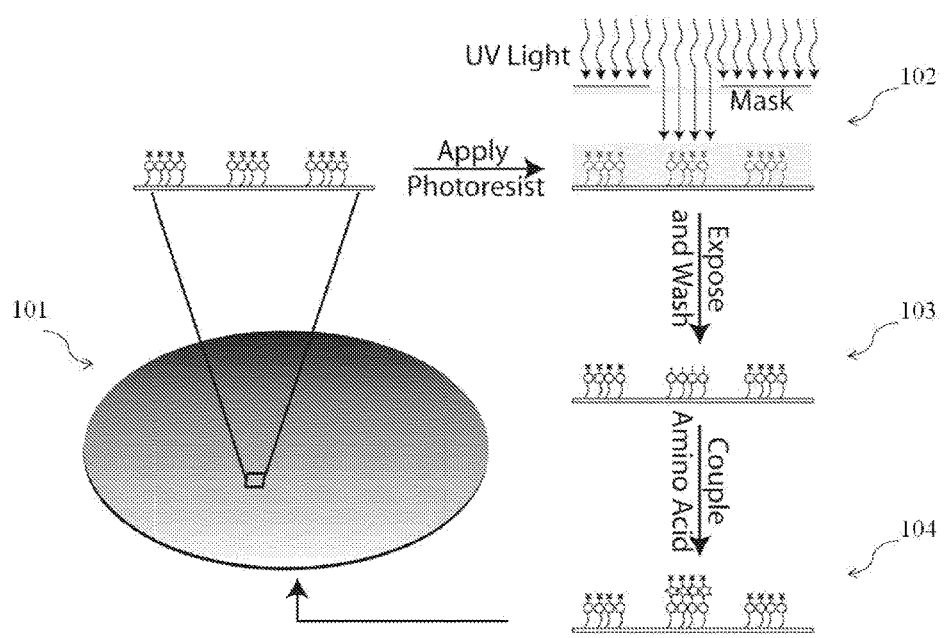
FIG. 1 illustrates a process pathway for fabrication of peptides on wafers.

There is increasing recognition that healthcare needs to move from post-symptomatic medicine to early detection and treatment of disease. However, it is challenging to develop systems that can proficiently diagnose early disease without a priori knowledge of the disease. An ideal system for the detection of early disease should be capable of identifying meaningful information from a biological sample in an unbiased manner.

Described herein are methods, processes, and protocols for in situ chemical patterning on surfaces that provide a reproducible and scalable platform for early disease diagnosis and health monitoring. The in situ synthesized chemical libraries of the invention are disease agnostic and can be synthesized without a priori awareness of a disease they are intended to diagnose. Specifically contemplated are methods, processes, and protocols to minimize the steps necessary to synthesize in situ chemical libraries on a surface or substrate. In some embodiments, the chemical libraries are randomized. In some embodiments, the chemical libraries are pseudo-random or semi-random. In some embodiments, the chemical libraries are synthesized irrespective of a target molecule. In some embodiments, peptide, nucleotide, saccharides, or other chemical arrays are synthesized in situ on a surface or substrate.

An in situ synthesized chemical library of the invention can be used to measure a plurality of parameters that reflect a state of health or a condition of a subject. The immune system can be a source of a biological sample(s) that detects a plurality of such parameters. The distinctive characteristics of antibody molecules suggest that methods which can identify, measure, and differentiate antibody molecules in a subject can provide systems for early detection and diagnosis of disease. As a consequence, in situ synthesized chemical libraries of the invention can be used to detect and identify a plurality of diseases for which a distinct antibody response develops.

Techniques for in situ synthesis of a variety of molecules, including oligonucleotides, peptides, ribonucleotides (RNA), polysaccharides, and other materials are known in the art. U.S. Pat. No. 5,424,186, hereinafter incorporated by reference in its entirety, describes techniques for forming high density arrays of, for example, oligonucleotides, and peptides, by sequentially removing a photoremovable group from a surface, coupling a monomer to the exposed region of the surface and repeating the process. The technology associated with this synthesis technique is known as "VLSIPS" or "Very Large Scale Immobilized Polymer Synthesis."

Other techniques for forming high density arrays of molecules on a surface or substrate include U.S. Pat. No. 5,384,261, which provides systems and methods for selectively deprotecting/coupling materials to a substrate; and U.S. Pat. No. 5,571,639, which describes the design of masks for fabricating high density arrays, both of which are incorporated herein by reference in its entirety. U.S. Pat. No. 6,153,743, which is incorporated herein by reference in its entirety, discloses methods and devices for more economically synthesizing arrays by use of shift reticles to reuse, and thus minimize, the number of photomasks needed for in situ synthesis of the arrays.

The methods and devices disclosed herein seek to economize the in situ synthesis of molecules on substrates, such as arrays, through the minimization of patterned chemical steps, including photomask, electrode-based, direct printing or other patterning means, used in the synthesis of these arrays. The minimized patterned steps create random, pseudorandom or semi-random arrays that could be used to create high-density, low-cost arrays. In some embodiments, the minimized patterned steps are used to synthesize arrays irrespective of the molecules to be targeted.

In some embodiments, an in situ synthesized chemical library, wherein said synthesis uses a minimum number of patterning steps to construct the library comprises:

Determining a number of patterned steps where M<R×N, wherein the number of patterned steps (M) is less than the number of patterned steps needed to synthesize a unique set of sequences (R×N, where R=the number of different monomer units, and N the length of the molecule);

Randomly assigning a clear (activated) or opaque (closed) designation at each feature position of each pattern for the array;

Randomly assigning a monomer to each pattern comprising a clear (activated) or opaque (closed) designation at each feature position;

Coupling monomers on the substrate at each clear location specified on each pattern; and Continuing monomer coupling for each pattern until the desired length or complexity of molecule is achieved.

The result of the above steps will not be perfectly random sequences, but it will be sequences that are substantially random. The degree of randomness depends in part on the total number of patterned steps, such as a photomasks patterned step, or the like. The greater number of patterned steps, the more random the sequences become.

The same number of patterned steps is optionally used for each feature on the substrate or array. Each feature designates physically separated areas on the area, wherein each feature contains identical molecules, e.g., identical peptides. In some instances, the same number of patterned steps is not used for each feature on the substrate or array. In such instances, the molecules generated at each feature may be made up of different numbers (or lengths) of monomers. To adjust for this occurrence, the algorithms disclosed herein can be modified by lifting the constraint that the total number of patterned steps in a set of patterns in which a particular feature is activated in the pattern must be exactly N. Instead, the probability of the feature being activated in each pattern of a set of patterns can be set to N/M, wherein N is the average number of monomers to be added to each feature (i.e. the number of coupling steps at each feature) and M is the total number of patterning steps.

As above, the total number of patterning steps can be reduced to a number less than N/M, which can be adjusted to remove the initial and later biases as described above.

A pseudorandom feature of the patterned chemical libraries disclosed herein is that the algorithms disclosed herein must start at position 1. Accordingly, position 1 will necessarily have a larger proportion of the first monomer added to it than randomness may dictate. This can be corrected by decreasing the fraction of the features to be activated in the first few and last few patterns used, and correspondingly increasing the fraction of features activated (clear) for patterns near the middle of the patterned chemical steps. For example, consider the creation of a library consisting of peptides with 10 different amino acids. One could create a series of masks that each randomly had 10% (0.1) of the features exposed and the rest not exposed. However, this would mean that the first amino acid added in the series would be present at the first position in the peptide 10% of the time, the second amino acid 90%×10%=9% (0.9× 0.1=0.09) of the time, the third amino acid 91%×90%× 10%=8.19% (0.91×0.9×0.1=0.0819) of the time, and in general the $n^{th}$ amino acid will be present a fraction of the time equaling $(1-P_a) \times 0.9 \times 0.1$. Thus the first position of the peptide will not have an even composition of the 10 amino acids. This can be partially mitigated by, for example, using a lower percentage of open features in the first mask, and/or using a slightly higher percentage in the second, although it may not possible to perfectly compensate for the bias.

In some embodiments the invention provides a kit. A kit can comprise a finger pricking device to draw a small quantity of blood from a subject and a receiving surface for the collection of the blood sample. In some embodiments, the kit comprises written instructions for a use thereof.

Chemical Libraries

Disclosed herein are methods and devices for reducing the number of patterning steps required to make random or randomized patterned chemical libraries, for example, with the cluster systems described above. It has become possible to create relatively large chemical libraries through in situ synthesis on solid surfaces forming patterns of synthetic molecules on said surfaces. Two types of chemical libraries currently made and sold commercially in this way include arrays of oligonucleotide libraries and peptide libraries. Commercial vendors of such in situ synthesized libraries include Nimblegen-Roche™, Affymetrix™, Agilent™, and LC Sciences™.

Other types of chemical libraries can be made using similar methods including peptide nucleic acid (PNA) libraries and other patterned chemical libraries on surfaces. The libraries do not have to be restricted to phosphodiester or amide bonds. Ester bonds, thioester bonds, ether bonds, carbon-carbon bonds are examples of other bonds that could be formed and many types of chemistry can be used to create these bonds, as has been demonstrated in general for solid phase synthesis and is well known to those in the art. The libraries synthesized in these ways do not have to be restricted to linear structures. Branched structures have been demonstrated and it is possible to add groups to an existing molecular scaffold as well. The monomer molecules used to make these in situ synthesized patterned chemical arrays do not have to be natural amino acids or nucleic acids. In fact they can be of a very broad range of chemical types. It is even possible to make patterned chemicals on surfaces using monomer molecules of different types and with different bonding connections. Patterning can be done using any of a large number of methods including photolithography acting on photolabile groups or photolithography acting on molecules that produce acid or base, or the use of electrodes to oxidize or reduce compounds or direct printing of chemicals onto surfaces containing the reactive compounds, or any of a number of other means of patterning compounds on a surface in such a way that they react to form new molecular species.

There are a number of applications or potential applications of in situ synthesized patterned chemical arrays in which either entirely or partially randomized additions of monomers are used. For example, one might create an in situ synthesized peptide library using patterned chemical means on a surface in which some or all of the sequence was varied randomly between the different patterned features on the surface. Applications for such random, randomized or pseudo-randomized libraries include, but are not limited to:

Diagnostic arrays;
Arrays for selection of specific ligands;
Arrays of potential drugs; and
Arrays of sensor molecules.

This approach involves creating a random, pseudo-randomized, or chemically defined array of peptides or peptide-like molecules on a surface, adding a diluted volume of serum, and detecting the pattern of bound antibodies to the different features on the peptide array. To say that a peptide sequence in a feature can be determined randomly means that while each feature in the patterned set of features on the surface contains a specific peptide sequence (or a group of defined peptide sequences), and that sequence (or sequences) are in general different from the sequence or sequences of most of the other features on the patterned surface, the sequence or sequences were determined by some means that introduced randomness into the sequence.

In general, to create a set of sequences (and here a sequence implies an order of attachment of monomer groups to create the final molecule, not necessarily a linear structure) of length N using one of R different monomer units at each point in the sequence requires R×N lithographic steps. For example, to create an array of peptides each of which was 15 amino acids in length using one of the 20 natural amino acids at each position would require 300 patterned synthetic steps.

In the case specifically where random or nearly random sequences, as defined above, at each feature are desired, it is possible to generate approximately random sequences with fewer than R×N steps. This can substantially decrease both the cost of generating an array and the time required to generate the array. The algorithm for performing this randomized or pseudorandom generation of sequences at the features of a chemical array is as follows:

Determine the number of photolithography steps, M, each corresponding to a mask.

Determine the number of features and the position of each feature in the mask. Each feature corresponds to a defined sequence of monomer additions (if only one monomer was added at each addition, this would result in a specific sequence at each feature).

Determine the number of additions to be made for each feature, N (this number may be different for each feature or it may be the same).

For each feature, distribute N open positions among the M masks randomly.

Consider a set of chemical features that each involves N patterned chemical couplings using one of R different monomer molecules. Consider the use of M steps to perform the patterned synthesis of the array where M<R×N. Each step requires the use of a pattern. The pattern defines a number of features. For N couplings, there will be M patterns. For each feature in the pattern, there must be N times when that feature is activated (N couplings at that feature). The N couplings are randomly distributed among the M patterns at that particular feature.

In some embodiments, the number of M steps to perform the patterned chemical couplings (patterned steps) is less than 10% R×N, is less than 15% R×N, less than 20% R×N, less than 25% R×N, less than 30% of R×N, less than 35% of R×N, less than 40% of R×N, less than 45% of R×N, less than 50% of R×N, less than 55% of R×N, less than 60% of R×N or less than 65% of R×N. In some embodiments, the number of M steps to perform the patterned chemical couplings is more than 35% R×N, more than 40% R×N, more than 45% R×N, more than 50% R×N, more than 55% R×N, more than 60% R×N, more than 65% R×N, more than 70% R×N, more than 75% R×N, more than 80% R×N, more than 85% R×N, more than 90% R×N or more than 95% R×N. In some embodiments, the number of M steps to perform the patterned chemical couplings is between about 35% to about 80% R×N, about 40% to about 75% R×N, about 45% to about 70% R×N, about 50% to about 65% R×N, or about 55% to about 60% R×N. In other embodiments, the number of M steps to perform the patterned chemical couplings is about 33% to about 95% R×N, about 51% to about 75% R×N, or about 51% to about 55% R×N. In other embodiments, the number of M steps to perform the patterned chemical couplings is about 35% R×N, about 40% R×N, about 45% R×N, about 50% R×N, about 55% R×N, about 60% R×N, about 65% R×N, about 70% R×N, about 75% R×N, about 80% R×N, about 85% R×N, about 90% R×N, or about 95% R×N. In yet other embodiments, the number of M steps to perform the patterned chemical couplings is about 51% R×N, about 52% R×N, about 53% R×N, about 54% R×N or about 55% R×N.

In some embodiments the minimum number of patterning steps, M, each corresponding to a patterned step is at least 15 steps, at least 16 steps, at least 17 steps, at least 18 steps, at least 19 steps, at least 20 steps, at least 21 steps, at least 22 steps, at least 23 steps, at least 24 steps, at least 25 steps, at least 26 steps, at least 27 steps, at least 28 steps, at least 29 steps, at least 30 steps, at least 31 steps, at least 32 steps, at least 33 steps, at least 34 steps, at least 35 steps, at least 36 steps, at least 37 steps, at least 38 steps, at least 39 steps, at least 40 steps, at least 41 steps, at least 42 steps, at least 43 steps, at least 44 steps, at least 45 steps, at least 46 steps, at least 47 steps, at least 48 steps, at least 49 steps, at least 50 steps, at least 51 steps, at least 52 steps, at least 53 steps, at least 54 steps, at least 55 steps, at least 56 steps, at least 57 steps, at least 58 steps, at least 59 steps, at least 60 steps, at least 61 steps, at least 62 steps, at least 63 steps, at least 64 steps, at least 65 steps, at least 66 steps, at least 67 steps, at least 68 steps, at least 69 steps, at least 70 steps, at least 71 steps, at least 72 steps, at least 73 steps, at least 74 steps, at least 75 steps, at least 76 steps, at least 77 steps, at least 78 steps, at least 79 steps, at least 80 steps, at least 81 steps, at least 82 steps, at least 83 steps, at least 84 steps, at least 85 steps, at least 86 steps, at least 87 steps, at least 88 steps, at least 89 steps, or at least 90 steps. In some embodiments the minimum number of patterning steps, M, is a minimum number of photomasking steps.

In some embodiments the minimum number of patterning steps, M, each corresponding to a patterned step is at most 15 steps, at most 16 steps, at most 17 steps, at most 18 steps, at most 19 steps, at most 20 steps, at most 21 steps, at most 22 steps, at most 23 steps, at most 24 steps, at most 25 steps, at most 26 steps, at most 27 steps, at most 28 steps, at most 29 steps, at most 30 steps, at most 31 steps, at most 32 steps, at most 33 steps, at most 34 steps, at most 35 steps, at most 36 steps, at most 37 steps, at most 38 steps, at most 39 steps, at most 40 steps, at most 41 steps, at most 42 steps, at most 43 steps, at most 44 steps, at most 45 steps, at most 46 steps, at most 47 steps, at most 48 steps, at most 49 steps, at most 50 steps, at most 51 steps, at most 52 steps, at most 53 steps, at most 54 steps, at most 55 steps, at most 56 steps, at most 57 steps, at most 58 steps, at most 59 steps, at most 60 steps, at most 61 steps, at most 62 steps, at most 63 steps, at most 64 steps, at most 65 steps, at most 66 steps, at most 67 steps, at most 68 steps, at most 69 steps, at most 70 steps, at most 71 steps, at most 72 steps, at most 73 steps, at most 74 steps, at most 75 steps, at most 76 steps, at most 77 steps, at most 78 steps, at most 79 steps, at most 80 steps, at most 81 steps, at most 82 steps, at most 83 steps, at most 84 steps, at most 85 steps, at most 86 steps, at most 87 steps, at most 88 steps, at most 89 steps, or at most 90 steps.

For example, an array of 1000 peptides can be synthesized using in situ patterned synthesis. Suppose that this is to be performed using photolithography and masks. Suppose further that the peptides are 10 amino acids long and that 5 different amino acids are used to make them. A perfectly random set of peptides could be generated by using a computer to determine random sequences at each of the 1000 features and then designing 5×10=50 masks that would pattern each of the 5 amino acids separately at each of the 10 positions in the peptide. However, a pseudo-random set of sequences can be created using 25 masks, or 50% of R×N. At each feature position in each mask, the mask is either clear or opaque. At each feature position in the mask set, 10 of the 25 masks are randomly assigned a clear value while the remainder are opaque. Each mask is then randomly assigned one of the 5 amino acids. The result will not be perfectly random sequences, but it will be sequences that are substantially random. The degree of randomness depends on the total number of masks (patterns, steps). The greater the number of masks, the more random the sequences become.

In some embodiments, the number of unique monomers R used in an in situ synthesized chemical library is fewer than 5 unique monomers, fewer than 6 unique monomers, fewer than 7 unique monomers, fewer than 8 unique monomers, fewer than 9 unique monomers, fewer than 10 unique monomers, fewer than 11 unique monomers, fewer than 12 unique monomers, fewer than 13 unique monomers, fewer than 14 unique monomers, fewer than 15 unique monomers, fewer than 16 unique monomers, fewer than 17 unique monomers, fewer than 18 unique monomers, fewer than 19 unique monomers, fewer than 20 unique monomers, fewer than 21 unique monomers, fewer than 22 unique monomers, fewer than 23 unique monomers, fewer than 24 unique monomers, fewer than 25 unique monomers, fewer than 26 unique monomers, fewer than 27 unique monomers, fewer than 28 unique monomers, fewer than 29 unique monomers, or fewer than 30 unique monomers.

In some embodiments, the unique monomers are chosen based upon a hierarchy of monomers that contribute favorably to the binding profile desired or obtained. For example, for peptide synthesis, it is possible to determine a generalized hierarchy of amino acids that will work best in obtaining acceptable immunosignature profiles. Aromatic and basic amino acids are generally desirable, followed by charged, polar and acidic amino acids, depending upon the target molecule or antibody. In other embodiments, redundant monomers can be eliminated as a candidate. For example, in some embodiments, isoleucine, which is generally present in the form of leucine, can be removed from the list of amino acids for incorporation into a peptide array. For the same reason threonine can also be removed from the list of amino acids for incorporation into a peptide array because of its similarity to serine. In some embodiments, monomers which contribute to undesirable secondary structure of the molecules generated (for example, secondary structures inducing cross-interaction of the molecules on the solid surface) are also omitted. For example, cysteine, which can form disulfide-bonds between neighboring cysteines, can induce undesirable secondary structure formations, which can lead to, for example, aggregation or clumping on the array surface.

One of the nonrandom features of this algorithm is that it must start at position 1. Therefore, position 1 will necessarily have a larger proportion of the first monomer added to it than randomness would dictate. This can be corrected by decreasing the fraction of the activated (e.g. clear) features in the first few and last few patterns used and correspondingly increasing the fraction of the features activated for patterns near the middle of the patterned chemical steps.

It is also not necessary to use the same number of steps at each of the features. This will result in molecules generated at each feature made up of different numbers of monomers. For many applications, this is not a detriment. The algorithm above can be easily modified by lifting the constraint that the total number of masks in the mask set in which a particular feature is activated must be exactly N. One can instead set the probability of the feature being activated in each mask of the mask set at N/M, where N is the average number of monomers to be added to each feature (the number of coupling steps at each feature) and M is the total number of patterning steps.

Setting the probability of each feature being activated in each mask of the mask set at N/M provides a granular, heterogeneous, quality to the total numbers of features in an in situ synthesized chemical library. Such granularity can allow a more adept representation of a proteome comprising heteropolymers of distinct lengths N in a single array. In some embodiments, an in situ synthesized chemical library comprises monomers of homogenous length N of 8 monomers, 9 monomers, 10 monomers, 11 monomers, 12 monomers, 13 monomers, 14 monomers, 15 monomers, 16 monomers, 17 monomers, 18 monomers, 19 monomers, or 20 monomers. In some embodiments, an in situ synthesized chemical library comprises heterogeneous monomers with a granular distribution of length. In some embodiments about 10% to about 15% of the monomers have a length N of 8; about 15% to about 20% of the monomers have a length N of 8; about 20% to about 25% of the monomers have a length N of 8; about 25% to about 30% of the monomers have a length N of 8; about 30% to about 35% of the monomers have a length N of 8; about 35% to about 40% of the monomers have a length N of 8; about 40% to about 45% of the monomers have a length N of 8; about 45% to about 50% of the monomers have a length N of 8; about 50% to about 55% of the monomers have a length N of 8; about 55% to about 60% of the monomers have a length N of 8; about 60% to about 65% of the monomers have a length N of 8; about 65% to about 70% of the monomers have a length N of 8; about 75% to about 80% of the monomers have a length N of 8; about 80% to about 85% of the monomers have a length N of 8; about 85% to about 90% of the monomers have a length N of 8; about 90% to about 95% of the monomers have a length N of 8; about 95% to about 100% of the monomers have a length N of 8.

In some embodiments about 10% to about 15% of the monomers have a length N of 9; about 15% to about 20% of the monomers have a length N of 9; about 20% to about 25% of the monomers have a length N of 9; about 25% to about 30% of the monomers have a length N of 9; about 30% to about 35% of the monomers have a length N of 9; about 35% to about 40% of the monomers have a length N of 9; about 40% to about 45% of the monomers have a length N of 9; about 45% to about 50% of the monomers have a length N of 9; about 50% to about 55% of the monomers have a length N of 9; about 55% to about 60% of the monomers have a length N of 9; about 60% to about 65% of the monomers have a length N of 9; about 65% to about 70% of the monomers have a length N of 9; about 75% to about 80% of the monomers have a length N of 9; about 80% to about 85% of the monomers have a length N of 9; about 85% to about 90% of the monomers have a length N of 9; about 90% to about 95% of the monomers have a length N of 9; about 95% to about 100% of the monomers have a length N of 9.

In some embodiments about 10% to about 15% of the monomers have a length N of 10; about 15% to about 20% of the monomers have a length N of 10; about 20% to about 25% of the monomers have a length N of 10; about 25% to about 30% of the monomers have a length N of 10; about 30% to about 35% of the monomers have a length N of 10; about 35% to about 40% of the monomers have a length N of 10; about 40% to about 45% of the monomers have a length N of 10; about 45% to about 50% of the monomers have a length N of 10; about 50% to about 55% of the monomers have a length N of 10; about 55% to about 60% of the monomers have a length N of 10; about 60% to about 65% of the monomers have a length N of 10; about 65% to about 70% of the monomers have a length N of 10; about 75% to about 80% of the monomers have a length N of 10; about 80% to about 85% of the monomers have a length N of 10; about 85% to about 90% of the monomers have a length N of 10; about 90% to about 95% of the monomers have a length N of 10; about 95% to about 100% of the monomers have a length N of 10.

In some embodiments about 10% to about 15% of the monomers have a length N of 11; about 15% to about 20% of the monomers have a length N of 11; about 20% to about 25% of the monomers have a length N of 11; about 25% to about 30% of the monomers have a length N of 11; about 30% to about 35% of the monomers have a length N of 11; about 35% to about 40% of the monomers have a length N of 11; about 40% to about 45% of the monomers have a length N of 11; about 45% to about 50% of the monomers have a length N of 11; about 50% to about 55% of the monomers have a length N of 11; about 55% to about 60% of the monomers have a length N of 11; about 60% to about 65% of the monomers have a length N of 11; about 65% to about 70% of the monomers have a length N of 11; about 75% to about 80% of the monomers have a length N of 11; about 80% to about 85% of the monomers have a length N of 11; about 85% to about 90% of the monomers have a length N of 11; about 90% to about 95% of the monomers have a length N of 11; about 95% to about 100% of the monomers have a length N of 11.

In some embodiments about 10% to about 15% of the monomers have a length N of 12; about 15% to about 20% of the monomers have a length N of 12; about 20% to about 25% of the monomers have a length N of 12; about 25% to about 30% of the monomers have a length N of 12; about 30% to about 35% of the monomers have a length N of 12; about 35% to about 40% of the monomers have a length N of 12; about 40% to about 45% of the monomers have a length N of 12; about 45% to about 50% of the monomers have a length N of 12; about 50% to about 55% of the monomers have a length N of 12; about 55% to about 60% of the monomers have a length N of 12; about 60% to about 65% of the monomers have a length N of 12; about 65% to about 70% of the monomers have a length N of 12; about 75% to about 80% of the monomers have a length N of 12; about 80% to about 85% of the monomers have a length N of 12; about 85% to about 90% of the monomers have a length N of 12; about 90% to about 95% of the monomers have a length N of 12; about 95% to about 100% of the monomers have a length N of 12.

In some embodiments about 10% to about 15% of the monomers have a length N of 13; about 15% to about 20% of the monomers have a length N of 13; about 20% to about 25% of the monomers have a length N of 13; about 25% to about 30% of the monomers have a length N of 13; about 30% to about 35% of the monomers have a length N of 13; about 35% to about 40% of the monomers have a length N of 13; about 40% to about 45% of the monomers have a length N of 13; about 45% to about 50% of the monomers have a length N of 13; about 50% to about 55% of the monomers have a length N of 13; about 55% to about 60% of the monomers have a length N of 13; about 60% to about 65% of the monomers have a length N of 13; about 65% to about 70% of the monomers have a length N of 13; about 75% to about 80% of the monomers have a length N of 13; about 80% to about 85% of the monomers have a length N of 13; about 85% to about 90% of the monomers have a length N of 13; about 90% to about 95% of the monomers have a length N of 13; about 95% to about 100% of the monomers have a length N of 13.5

In some embodiments about 10% to about 15% of the monomers have a length N of 14; about 15% to about 20% of the monomers have a length N of 14; about 20% to about 25% of the monomers have a length N of 14; about 25% to about 30% of the monomers have a length N of 14; about 30% to about 35% of the monomers have a length N of 14; about 35% to about 40% of the monomers have a length N of 14; about 40% to about 45% of the monomers have a length N of 14; about 45% to about 50% of the monomers have a length N of 14; about 50% to about 55% of the monomers have a length N of 14; about 55% to about 60% of the monomers have a length N of 14; about 60% to about 65% of the monomers have a length N of 14; about 65% to about 70% of the monomers have a length N of 14; about 75% to about 80% of the monomers have a length N of 14; about 80% to about 85% of the monomers have a length N of 14; about 85% to about 90% of the monomers have a length N of 14; about 90% to about 95% of the monomers have a length N of 14; about 95% to about 100% of the monomers have a length N of 14.

In some embodiments about 10% to about 15% of the monomers have a length N of 15; about 15% to about 20% of the monomers have a length N of 15; about 20% to about 25% of the monomers have a length N of 15; about 25% to about 30% of the monomers have a length N of 15; about 30% to about 35% of the monomers have a length N of 15; about 35% to about 40% of the monomers have a length N of 15; about 40% to about 45% of the monomers have a length N of 15; about 45% to about 50% of the monomers have a length N of 15; about 50% to about 55% of the monomers have a length N of 15; about 55% to about 60% of the monomers have a length N of 15; about 60% to about 65% of the monomers have a length N of 15; about 65% to about 70% of the monomers have a length N of 15; about 75% to about 80% of the monomers have a length N of 15; about 80% to about 85% of the monomers have a length N of 15; about 85% to about 90% of the monomers have a length N of 15; about 90% to about 95% of the monomers have a length N of 15; about 95% to about 100% of the monomers have a length N of 15.

In some embodiments about 10% to about 15% of the monomers have a length N of 16; about 15% to about 20% of the monomers have a length N of 16; about 20% to about 25% of the monomers have a length N of 16; about 25% to about 30% of the monomers have a length N of 16; about 30% to about 35% of the monomers have a length N of 16; about 35% to about 40% of the monomers have a length N of 16; about 40% to about 45% of the monomers have a length N of 16; about 45% to about 50% of the monomers have a length N of 16; about 50% to about 55% of the monomers have a length N of 16; about 55% to about 60% of the monomers have a length N of 16; about 60% to about 65% of the monomers have a length N of 16; about 65% to about 70% of the monomers have a length N of 16; about 75% to about 80% of the monomers have a length N of 16; about 80% to about 85% of the monomers have a length N of 16; about 85% to about 90% of the monomers have a length N of 16; about 90% to about 95% of the monomers have a length N of 16; about 95% to about 100% of the monomers have a length N of 16.

In some embodiments about 10% to about 15% of the monomers have a length N of 17; about 15% to about 20% of the monomers have a length N of 17; about 20% to about 25% of the monomers have a length N of 17; about 25% to about 30% of the monomers have a length N of 17; about 30% to about 35% of the monomers have a length N of 17; about 35% to about 40% of the monomers have a length N of 17; about 40% to about 45% of the monomers have a length N of 17; about 45% to about 50% of the monomers have a length N of 17; about 50% to about 55% of the monomers have a length N of 17; about 55% to about 60% of the monomers have a length N of 17; about 60% to about 65% of the monomers have a length N of 17; about 65% to about 70% of the monomers have a length N of 17; about 75% to about 80% of the monomers have a length N of 17; about 80% to about 85% of the monomers have a length N of 17; about 85% to about 90% of the monomers have a length N of 17; about 90% to about 95% of the monomers have a length N of 17; about 95% to about 100% of the monomers have a length N of 17.

In some embodiments about 10% to about 15% of the monomers have a length N of 18; about 15% to about 20% of the monomers have a length N of 18; about 20% to about 25% of the monomers have a length N of 18; about 25% to about 30% of the monomers have a length N of 18; about 30% to about 35% of the monomers have a length N of 18; about 35% to about 40% of the monomers have a length N of 18; about 40% to about 45% of the monomers have a length N of 18; about 45% to about 50% of the monomers have a length N of 18; about 50% to about 55% of the monomers have a length N of 18; about 55% to about 60% of the monomers have a length N of 18; about 60% to about 65% of the monomers have a length N of 18; about 65% to about 70% of the monomers have a length N of 18; about 75% to about 80% of the monomers have a length N of 18; about 80% to about 85% of the monomers have a length N of 18; about 85% to about 90% of the monomers have a length N of 18; about 90% to about 95% of the monomers have a length N of 18; about 95% to about 100% of the monomers have a length N of 18.

Molecular Libraries.

In some embodiments, the randomized or pseudo-randomized chemical libraries include oligonucleotide libraries and peptide libraries. In some embodiments the randomized or pseudo-randomized chemical libraries include peptide nucleic acid (PNA) libraries or oligosaccharide libraries. In some embodiments, the libraries comprise molecules comprising phosphodiester or amide bonds. In some embodiments, the libraries comprise molecules comprising ester bonds, thioester bonds, ether bonds, carbon-carbon bonds or other bonds that are used for solid phase synthesis of polymer arrays.

In some embodiments, in situ synthesis of peptides on a substrate is contemplated, wherein the peptide synthesized is about 5 amino acids to about 30 amino acids, about 10 amino acids to about 25 amino acids, about 10 amino acids to about 20 amino acids, about 15 amino acids to about 20 amino acids. In some embodiments, peptides of about 10 amino acids, of about 11 amino acids, of about 12 amino acids, of about 13 amino acids, of about 14 amino acids, of about 15 amino acids, of about 16 amino acids, of about 17 amino acids, of about 18 amino acids, of about 19 amino acids, of about 20 amino acids, of about 21 amino acids, of about 22 amino acids, of about 23 amino acids, of about 24 amino acids or of about 25 amino acids are manufactured using the methods described herein.

In some embodiments, in situ synthesis of nucleotides on a substrate surface is contemplated, wherein the nucleotide synthesized in situ is about 2 nucleic acids to about 5 nucleic acids, about 2 nucleic acids to about 10 nucleic acids, about 2 nucleic acids to about 25 nucleic acids, about 2 nucleic acids to about 40 nucleic acids, about 2 nucleic acids to about 50 nucleic acids, about 5 nucleic acids to about 25 nucleic acids, about 5 nucleic acids to about 40 nucleic acids, about 5 nucleic acids to about 50 nucleic acids, about 10 nucleic acids to about 40 nucleic acids, or about 10 nucleic acids to about 25 nucleic acids. In some embodiments, the nucleotides contemplated herein are about 5 nucleic acids, about 10 nucleic acids, about 15 nucleic acids, about 20 nucleic acids or more.

In some embodiments, in situ synthesis of peptide nucleic acids (PNA) on a substrate surface is contemplated, wherein the PNA molecule synthesized in situ is about 2 PNAs to about 5 PNAs, about 2 PNAs to about 10 PNAs, about 2 PNAs to about 25 PNAs, about 2 PNAs to about 40 PNAs, about 2 PNAs to about 50 PNAs, about 5 PNAs to about 25 PNAs, about 5 PNAs to about 40 PNAs, about 5 PNAs to about 50 PNAs, about 10 PNAs to about 40 PNAs, or about 10 PNAs to 25 about PNAs. In some embodiments, the PNA molecules contemplated herein are about 5 PNAs, about 10 PNAs, about 15 PNAs, about 20 PNAs in length or more.

Instrumentation and Devices.

An in situ synthesized chemical library can be fabricated with robotic cluster systems. Included for use in the methods, systems, and processes disclosed herein are descriptions of exemplary robotic cluster systems for chemical patterning with micron resolution on wafer systems, including but not limited to 6-8 inch wafers. One example of a cluster system is the P900 cluster system from C& D Semiconductor Services Inc. (San Jose, Calif.) and a Model A 5008A aligner/exposure unit from Optical Associates Incorporated (San Jose, Calif.). This instrument is largely automated in terms of wafer handling, liquid dispense and alignment/exposure, allowing large number of lithography and coupling steps involved in many of synthesis steps performed, for example, 100-300 lithography/coupling steps per wafer. The cluster system can consist of modules that are standard in the industry, and the cluster system can consist of modules that are configured and programmed for specific chemical patterning processes. Non-limiting examples of modules include spin coater, hot plates, cold plates, robotic arm, dispense systems, aligner/exposure module).

A typical synthesis run on the cluster systems disclosed can require about 25-80 hours of 4 cycles per hour; up to 4 wafers can be processed simultaneously on these cluster systems. In some embodiments, the photolithography-based synthesis of the chemical libraries uses a minimum number of photomasks to construct the chemical library. In some embodiments, the photomasks comprise a feature of about 0.5 micron to about 200 microns in diameter and a center-to-center distance of about 1 micron to about 300 microns on center.

The lithography can be performed with masks (proximity or contact), of which about at least 50,000 individually defined molecules; at least 100,000 individually defined molecules; at least 500,000 individually defined molecules; at least 100,000 individually defined molecules; at least 250,000 individually defined molecules; at least 500,000 individually defined molecules; at least 750,000 individually defined molecules; at least 1,000,000 individually defined molecules; at least 10,000,000 individually defined molecules; at least 50,000,000 individually defined molecules; at least 100,000,000 individually defined molecules; or at least 150,000,000 individually defined molecules can be fabricated. The fabrication can take place on a wafer, for example, an 8-inch wafer, in some embodiments using 4 micron features, 5 micron features, 6 micron features, 7 micron features, 8 micron features, 9 micron features, 10 micron features, 11 micron features, 12 micron features, 13 micron features, 14 micron features or 15 micron features. In some embodiments, the fabrication can take place on a wafer, for example, an fl-inch wafer, using a center-to-center distance of 5 microns on center, 6 microns on center, 7 microns on center, 8 microns on center, 9 microns on center, 10 microns on center, 11 microns on center, 12 microns on center, 13 microns on center, 14 microns on center, 15 microns on center, 16 microns on center, 17 microns on center, 18 microns on center, 19 microns on center or 20 microns on center. The feature and center size dimensions are chosen to allow space for dicing as well as later quality control analysis on the fabricated array.

Also disclosed herein are methods and devices for making and using patterned chemical surfaces, for fabrication and application of chemical arrays, including nucleotide, peptide, and other chemical arrays. In some embodiments, the patterned chemical process includes spotting pre-synthesized peptides on glass slides using either contact or piezoelectric approaches (10,000 peptide features per array). In some embodiments, in situ synthesized chemical synthesis are used which allow 330,000 chemical features to be fabricated per array. In other embodiments, in situ synthesized chemical synthesis are used which allow 1,000,000 chemical features to be fabricated per array. A schematic of an in situ synthesis process is shown in FIG. 1. Advantages of in situ synthesis processes can include:

Robust Processes;
Reproducibility: in situ synthesis is more reproducible from peptide to peptide and from array to array as well as over time than is peptide printing, largely due to solubility issues.
Scalability: in situ synthesis can be done in a smaller scale, it can be cheaper and faster—The production of peptide wafers via the in situ fabrication approach, on for example, electronic wafers, can provide an in situ synthesized chemical library with higher density, rapid production scalability, and lower costs;
Electronic Integration: chemical array fabrication in situ can be directly integrated with the fabrication of underlying electronics for sensing, actuation, and analysis.
Flexibility: an in situ synthesized chemical library can use a minimum number of patterning steps, for example, a minimum number of photomasking steps. The photolithographic aspect of the process involves generating an acid in a local position to remove an acid labile protective group such as Boc or Trityl. The option of combining a number of patterning steps can be applicable to a very broad range of chemical syntheses.

In some embodiments, wafers are used which incorporate multiple microscope slide-sized regions. In some embodiments, the wafers are at least 1 inch in diameter, at least 2 inches in diameter, at least 4 inches in diameter, at least 5 inches in diameter, at least 6 inches in diameter, at least 8 inches in diameter, at least 10 inches in diameter, at least 12 inches in diameter, at least 16 inches in diameter, or at least 20 inches in diameter.

In some embodiments, the wafers are at least 1 inch to 20 inches in diameter, at least 2 inches to 16 inches in diameter, at least 3 inches to 12 inches in diameter or at least 4 inches to 12 inches in diameter. In some embodiments, the wafers are 12 inches in diameter. In some embodiments, the wafers are divided into at least 2 microscope slide-sized regions, at least 4 microscope slide-sized regions, at least 5 microscope slide-sized regions, at least 6 microscope slide-sized regions, at least 7 microscope slide-sized regions, at least 8 microscope slide-sized regions, at least 9 microscope slide-sized regions, at least 10 microscope slide-sized regions, at least 11 microscope slide-sized regions, at least 12 microscope slide-sized regions, at least 13 microscope slide-sized regions, at least 14 microscope slide-sized regions, at least 15 microscope slide-sized regions, at least 20 microscope slide-sized regions, at least 25 microscope slide-sized regions, at least 30 microscope slide-sized regions, at least 35 microscope slide-sized regions, at least 40 microscope slide-sized regions, or at least 45 microscope slide-sized regions. In some embodiments, each wafer comprises 13 microscope slide-sized regions. In some embodiments, the slide-sized regions are at least 1 inch in length, at least 2 inches in length, at least 3 inches in length, at least 4 inches in length, or at least 5 inches in length.

In some embodiments, the substrate (surface) of the microscope slide-sized region comprises an array. In some embodiments, the surface of the microscope slide-sized regions each contain at least 2 arrays, at least 4 arrays, at least 6 arrays, at least 8 arrays, at least 12 arrays, at least 16 arrays, at least 20 arrays, at least 22 arrays, at least 24 arrays, at least 28 arrays or at least 30 arrays. In some embodiments, each microscope slide-sized regions contains 24 arrays or more. In some embodiments, each array can cover at least a 0.01 $cm^2$ area, at least 0.05 $cm^2$ area, at least a 0.1 $cm^2$ area, at least a 0.2 $cm^2$ area, at least 0.3 $cm^2$ area, at least 0.4 $cm^2$ area, at least 0.5 $cm^2$, at least 0.6 $cm^2$ area, at least 0.8 $cm^2$ area, at least 1.0 $cm^2$ area, at least 1.2 $cm^2$ area, at least 1.5 $cm^2$ area or at least 2.0 $cm^2$ area.

In some embodiments, the surface contains at least 5,000 chemical features, at least 10,000 chemical features, at least 50,000 chemical features, at least 100,000 chemical features, at least 150,000 chemical features, at least 200,000 chemical features, at least 250,000 chemical features, at least 300,000 chemical features, at least 350,000 chemical features, at least 400,000 chemical features, at least 500,000 chemical features or at least 1,000,000 chemical features. In other embodiments, the array contains about 250,000 chemical features, about 300,000 chemical features, about 350,000 chemical features, about 400,000 chemical features, about 500,000 chemical features or about 600,000 chemical features. In some embodiments, the surface contains 330,000 chemical features, or a total of about 8 million chemical features per slide.

In some embodiments, the chemical features of the array are at least 0.5 micron in diameter, at least 1 micron in diameter, at least 2 microns in diameter, at least 3 microns in diameter, at least 4 microns in diameter, at least 5 microns in diameter, at least 6 microns in diameter, at least 7 microns in diameter, at least 8 microns in diameter, at least 9 microns in diameter, at least 10 microns in diameter, at least 12 microns in diameter, at least 15 microns in diameter, at least 30 microns in diameter, at least 100 microns in diameter or at least 200 microns in diameter. In some embodiments the chemical features of the array are about 0.5 micro to about 200 microns in diameter.

In other embodiments, the peptide feature is at least 1 micron on center, at least 2 microns on center, at least 3 microns on center, at least 4 microns on center, at least 5 microns on center, at least 6 microns on center, at least 7 microns on center, at least 8 microns on center, at least 9 microns on center, at least 10 microns on center, at least 13 microns on center at least 15 microns on center, at least 20 microns on center, at least 30 microns on center, at least 60 microns on center, at least 150 microns on center or at least 300 microns on center. In still other embodiments, the chemical features is about 1 to about 300 microns on center. In other embodiments, the chemical features of the array are 8 microns in diameter and 13 microns on center.

In other embodiments, the array contains at least 5,000 peptides, at least 10,000 peptides, at least 50,000 peptides, at least 100,000 peptides, at least 150,000 peptides, at least 200,000 peptides, at least 250,000 peptides, at least 300,000 peptides, at least 350,000 peptides, at least 400,000 peptides, at least 500,000 peptides or at least 1,000,000 peptides. In other embodiments, the array contains about 250,000 peptides, about 300,000 peptides, about 350,000 peptides, about 400,000 peptides, about 500,000 peptides or about 600,000 peptides. In some embodiments, the array contains 330,000 peptides, or a total of about 8 million peptides per slide.

In some embodiments, once diced into microscope slide-shaped pieces, each array on the slide can be individually assayed using a commercially available gasket system and plate washer. In some embodiments, peptide arrays consisting of peptides that are about 10-20 amino acids in length with a feature density of about 660,000/$cm^2$ on 8 inch silicon wafers are manufactured using the methods described herein.

Applications.

Described herein are processes utilizing in situ chemical synthesis, materials engineering, computational chemistry, and programmed molecular assembly to create chemical, biochemical and hybrid electronic systems with a high complexity and diversity of function. Processes and methods utilizing an in situ synthesized chemical library of the invention can be used to diagnose a plurality of conditions and to monitor a state of health.

Also described herein are micro and macro devices capable of recognizing complex molecular interactions. The in situ synthesized chemical libraries of the invention can map complex molecular interactions from complex chemical and biological mixtures. The in situ synthesized chemical libraries of the invention can detect signal transduction functions of a molecule at the surface of a cell, and the in situ synthesized chemical libraries of the invention can detect and measure pluralities of response functions and molecular interactions encompassed by the immune system. Also described herein are devices and methods that mimic complex synthetic systems by detecting interactions and binding of a sample with randomized or pseudo-randomized peptide arrays.

To accomplish the methods described herein arrays can be fabricated and characterized to create complex arrangements of functional molecular elements integrated into materials and electronics with high spatial resolution, either directly for the creation of chem/bio/electronic devices or as a means of searching large, intelligently designed libraries of molecules and complexes that can then serve as the functional elements of nanostructured systems. Molecular modeling can provide an in situ synthesized chemical libraries and methods without a priori knowledge of an antigenic nature of the synthesized peptides. The methods and processes described herein can be applied to complex functional characterizations like molecular recognition of macromolecules or catalysis. The methods and processes described herein can be coupled with high throughput synthesis and in situ screening of molecular function of the synthesized peptide.

An in situ synthesized chemical library of the invention can provide a method of early-detection of a condition of a subject. A condition of a subject can be a healthy condition or a disease condition. A condition can be an abnormal growth, e.g. cancer or an infection. Non-limiting examples of cancers that can be diagnosed, monitored, prevented, and/or treated with an array and a method of the invention can include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell cancer, stomach cancer, T-cell lymphoma, throat cancer, thymoma, thymic carcinoma, thyroid cancer, trophoblastic tumor (gestational), cancers of unkown primary site, urethral cancer, uterine sarcoma, vaginal cancer, vulvar cancer, Waldenström macroglobulinemia, and Wilms tumor.

In some embodiments, an in situ synthesized chemical library of the invention can provide a method of early-detection of a disease associated with the immune system. Non-limiting examples of diseases associated with the immune system can include: auto-immune disorders, inflammatory diseases, HIV, rheumatoid arthritis, diabetes mellitus type 1, systemic lupus erythematosus, scleroderma, multiple sclerosis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, autoimmune lymphoproliferative syndrome, Wiskott-Aldrich syndrome, chronic granulomatous disease, common variable immunodeficiency (CVID), hyperimmunoglobulin E syndrome, and Hashimoto's thyroiditis.

In some embodiments, the inflammatory disease or disorder generally refers to any disorders associated with inflammatory response abnormalities. Non-immune diseases with etiological origins in inflammatory processes include, e.g., cancer, cardiovascular disorders, neurological disorders, gastrointestinal disorders, metabolic disorders, among others. Non-limiting examples of inflammatory disorders include, e.g., asthma, aortic valve stenosis, celiac disease, chronic prostatitis, glomerulonephritis, hypersensitivities, inflammatory bowel diseases, lupus, multiple sclerosis, pelvic inflammatory disease, reperfusion injury, arthritis, rheumatoid arthritis, fibromyalgia, sarcoidosis, transplant rejection, vasculitis, and interstitial cystitis, among others.

Also disclosed herein are methods and devices for using patterned chemical synthesis, including but not limited to lithography, to develop enhanced methods to fabricate and interrogate millions of specifically designed molecules in ordered libraries on surfaces including electronic media. In situ synthesized chemical libraries can contribute to the development of new diagnostics and therapeutics. In situ synthesized chemical libraries can be synthesized on a substrate that is coupled with electronic devices.

Design and Construction of Peptide Immunosignaturing Arrays on Wafers.

A process of in situ chemical patterning of a surface, such as an array surface, is shown schematically in FIG. 1. FIG. 1 is a schematic depicting a the fabrication of an array on a silicon wafer. The surface of a silicon wafer is covalently modified to provide attachment groups, for example amine or hydroxyl attachment groups 101. A thermal oxide-coated silicon wafer surface is derivatized with a monolayer of amino silane to create the peptide attachment sites and Boc-glycine is uniformly attached to the surface 101. A photoresist, containing a photoacid generator, is spun onto the wafer and exposed through a mask to 365 nm light, resulting in the patterned deprotection of Boc-protected amines in specific features of the array 102. UV light is patterned onto the wafer generating localized acid which in turn removes the blocking groups from particular features 103. A coupling solution containing an amino acid is next spun onto the wafer and coupling takes place only at the deprotected features. The surface of the wafer is washed with a suitable solution 104. An amino acid or some other building block is coupled to the unprotected features 105. The process is then repeated, successively synthesizing specific heteropolymers on different features. Similar approaches can be used for a variety of chemistries involving acid labile blocking groups. Peptide synthesis on silicon wafers has been generally described by Price J V, Tangsombatvisit S, Xu G, et al. On silico peptide microarrays for high-resolution mapping of antibody epitopes and diverse protein-protein interactions. *Nat Med.* 2012; US 2009/0258796 A and US 2007/0122842, incorporated herein by reference for generalized teaching of peptide synthesis.

The heteropolymers synthesized on the array, or on a surface, can have identical lengths or can vary in length, depending upon the patterned masks used.

For example, the heteropolymers synthesized on the array can be peptides of different peptide lengths, with an average length distribution throughout the array. In this specific example, a distribution of peptide lengths can be generated averaging 12 amino acids long with peptides at each individual feature ranging from, for example, 8-17 amino acids. The sequence of each peptide can be pseudorandomly generated using an algorithm that minimizes the number of synthetic cycles required.

In some embodiments, only certain amino acids are used in the generation of the peptide arrays disclosed herein. For example, a pseudorandom algorithm can use 16 of the 20 natural amino acids, with cysteine, methionine, isoleucine, and threonine excluded. In some embodiments, the amino acids chosen for in situ synthesis and incorporation includes at least tryptophan. In some embodiments, the peptide arrays disclosed herein can use at least 10 of the natural amino acids, at least 12 of the natural amino acids, at least 13 of the natural amino acids, at least 14 of the natural amino acids, at least 15 of the natural amino acids, at least 16 of the natural amino acids, at least 17 of the natural amino acids, at least 18 of the natural amino acids, at least 19 of the natural amino acids or at least 20 of the natural amino acids.

Figure 2:
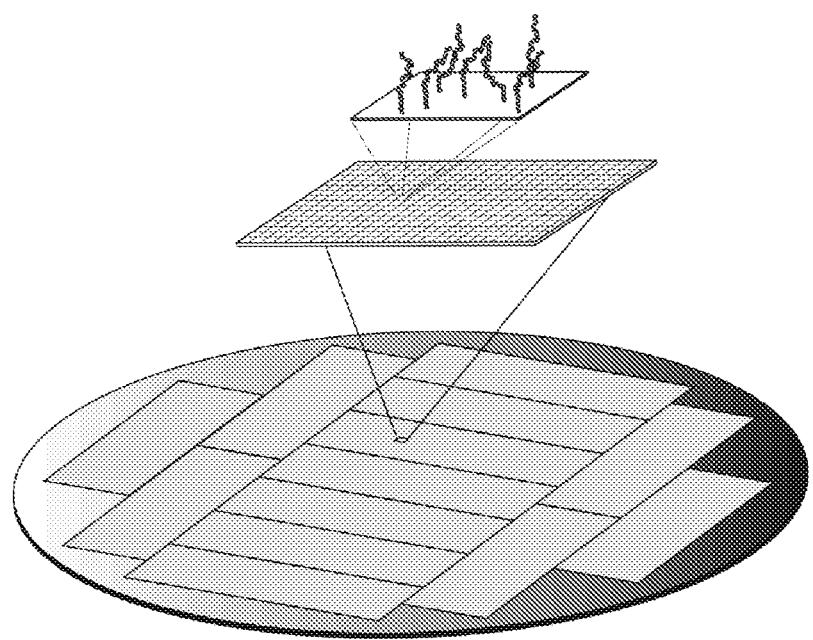
FIG. 2 is a diagram of a representative wafer layout.

FIG. 2 is an illustration of an exemplary wafer layout. A wafer can be divided into a plurality of divisions, or pieces. In one embodiment, the wafer is diced into 13 pieces, each with approximate dimensions of a microscope slide. The peptides can be arrayed on, for example, 13 slides on a wafer that has 13 divisions. Pluralities of arrays were synthesized with this method. For example, an array fabricated with the method described herein consisted of 330,000 peptide features wherein each feature is 8 microns in diameter and 13 microns on center. There can be a total of about 8 million features per slide. The method described herein allows production of an array comprising the described features in 90 lithography cycles (plus pre/post processing) at about 20 minutes per cycle. Each array fabricated on the slide can be individually assayed using a commercial gasket system and plate washer. The regions outside of the slides on the wafer can be used for quality control. The regions can have 200 micron features, and the regions can be assayed with MALDI TOF imaging spectrometry to determine the quality and reproducibility of the synthesized arrays.

EXAMPLES

Example 1: In Situ Synthesis and Analysis of Chemical Libraries

An in situ synthesized chemical library using a minimum number of patterning steps to construct the library as described herein can produce highly reproducible arrays of peptides that are both chemically consistent from array to array and accessible for antibody binding. An in situ synthesized chemical library can bind to antibodies from a blood sample of a subject, and an in situ synthesized chemical library can be used to detect an immunosignature.

Figure 3:
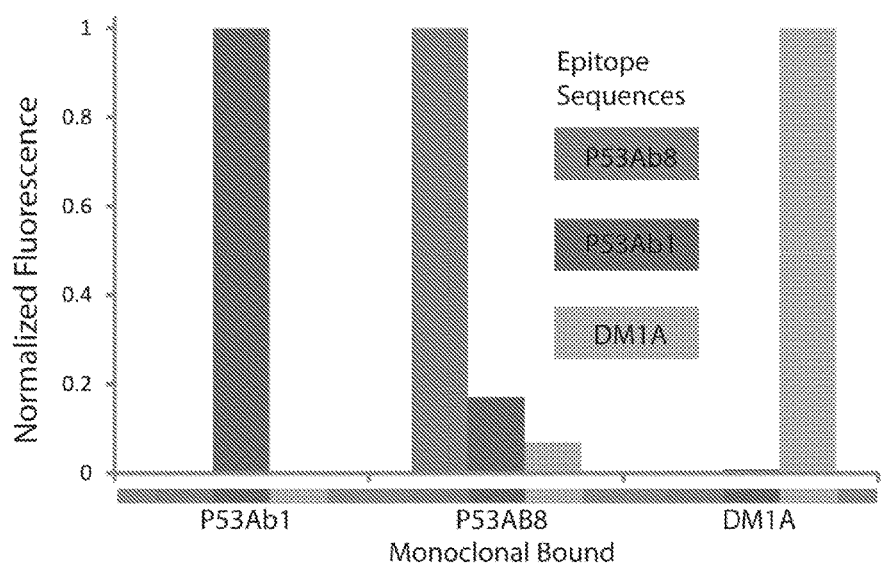
FIG. 3 is a graphical representation of the binding of monoclonal antibodies to a peptide array.

The chemical purity and yield of synthesis of peptides on the arrays can be analyzed by generating 200 micron test features on the same wafers used to fabricate the arrays and performing MALDI (matrix-assisted laser desorption ionization) mass spectrometry imaging. FIG. 3 is a graphical quantization of mass spectra of three of the features, each a variant of the epitope for the monoclonal antibody DM1A demonstrating that the sequences were generated as intended. FIG. 3 shows a bar graph depicting the relative binding of three different monoclonal antibodies to their cognate epitopes and to the epitopes of the other two antibodies. Cognate epitopes for monoclonal antibodies p53Ab8 (epitope: SDLWKL), p53Ab1 (RHSVV), and DM1A (AALEKD) were synthesized 2163 times as part of the 330,000 feature array. Average binding levels of each monoclonal antibody (Ab probe) with each epitope (nine measurements) are shown and normalized to binding to the cognate epitope in FIG. 3. The first (leftmost) set of bars corresponds to intensities on the array when the monoclonal antibody P53Ab1 was bound. The monoclonal antibody P53Ab1 binds only to its cognate sequence (the red bars represent binding to the P53Ab1 epitope sequence on the array). The binding of monoclonal antibody P53Ab1 to the other two cognate sequences was insignificant, and it is not visualized on this graph. Similarly, P53Ab8 (middle), and DM1A (right) monoclonals each bind most strongly to their cognate sequences (blue and green, respectively).

Figure 4:
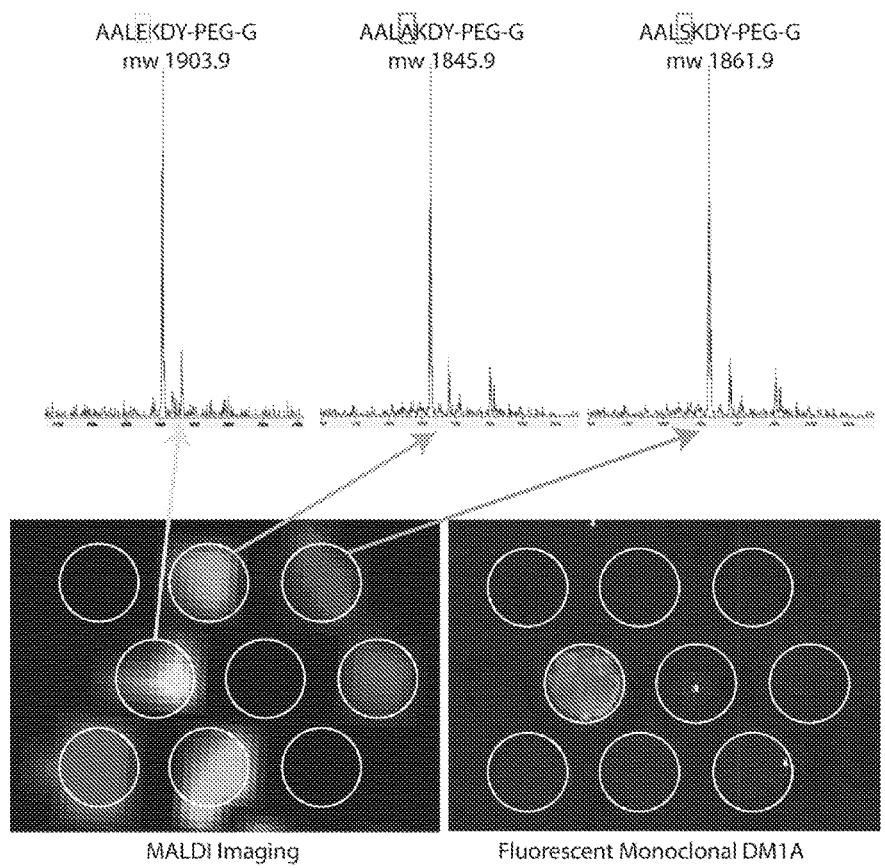
FIG. 4 illustrates a MALDI spectrometry imaging and a Fluorescent imaging of the binding of a monoclonal antibody to a peptide arrays.

In the array evaluated herein, peptides were synthesized on a region of a wafer as 200 micron spots, and both binding of a fluorescently labeled monoclonal antibody (lower right) and imaging MALDI spectrometry (lower left) were performed. This analysis was performed directly on surface features, but not in the slide-shaped regions. Instead, outside of the slide-shaped regions on the wafer, larger, 200 micron QC features were created and these were used for the analysis of FIG. 4. FIG. 4 shows a MALDI (Matrix-Assisted Laser Desorption Ionization) mass spectrum image (lower right, different colors represent different molecular weights), the corresponding monoclonal binding (lower right, only the cognate peptide shows significant binding) and the mass spectra of several of the features (top three mass spectra). The colors represent different molecular weights. One of the peptides synthesized on the array (yellow on the left image) corresponds to a specific epitope for a monoclonal antibody (DM1A). The synthesized peptide bound a fluorescently labeled version of that antibody (bottom right). The green, dark purple and yellow regions on the lower left panel are three variants of the DM1A epitope AALEKDY (one cognate, one with A substituted for E and one with S substituted—each color represents a different molecular weight). These epitopes were made using glycine-polyethylene glycol (G-PEG) as a linker. The mass spectra of three of the features was determined directly from the surface by cleaving the peptide from the surface without diffusion using a gas cleavage reagent and then performing the imaging mass spectrometry. Each of the peptide features has a peptide with the expected molecular weight. MALDI spectra extracted from several of the imaged features over a 160 Dalton mass range are provided. The small peak to the right of the main peak represents incomplete side-chain deprotection FIG. 4.

Figure 5:
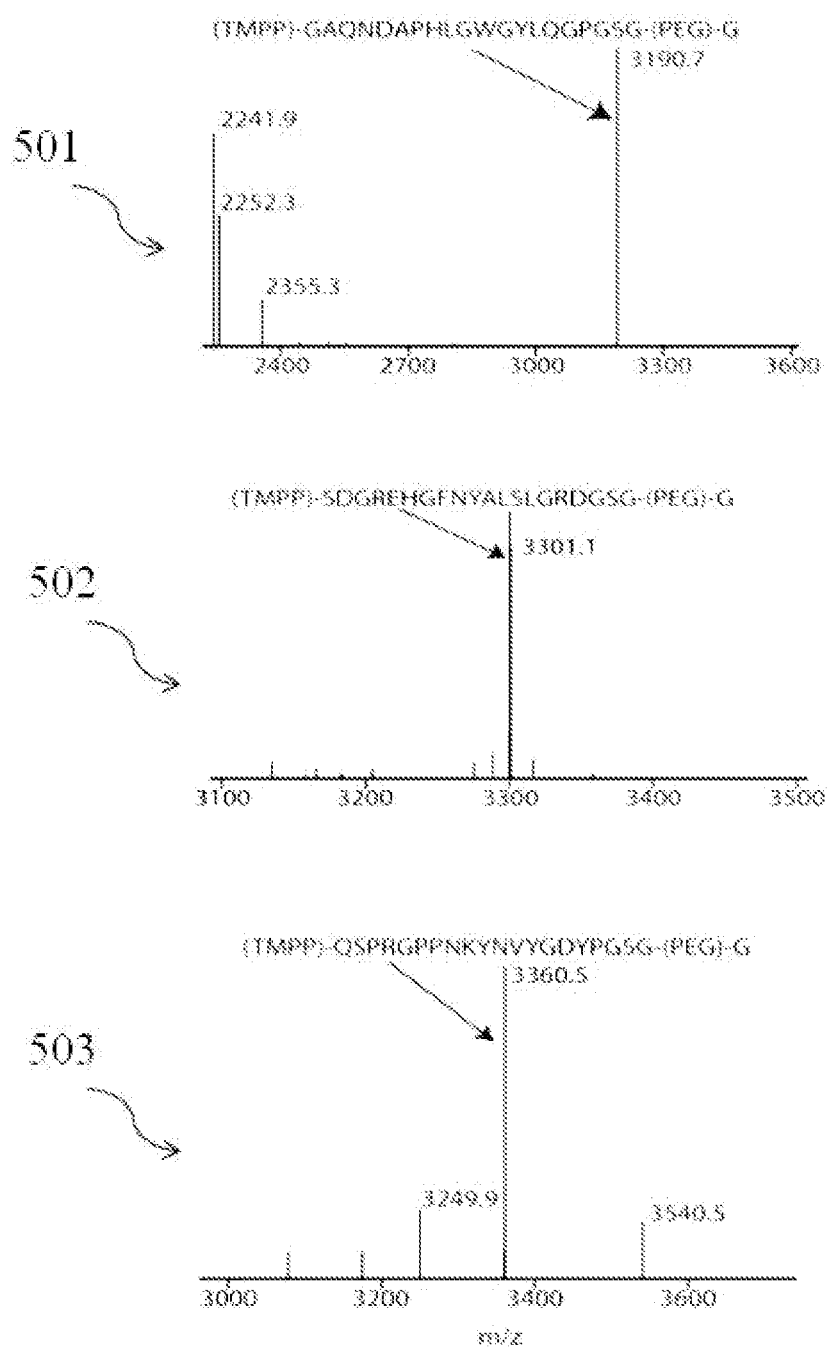
FIG. 5 is an illustration of MALDI spectra analysis from individual 200 micron features.
Figure 6:
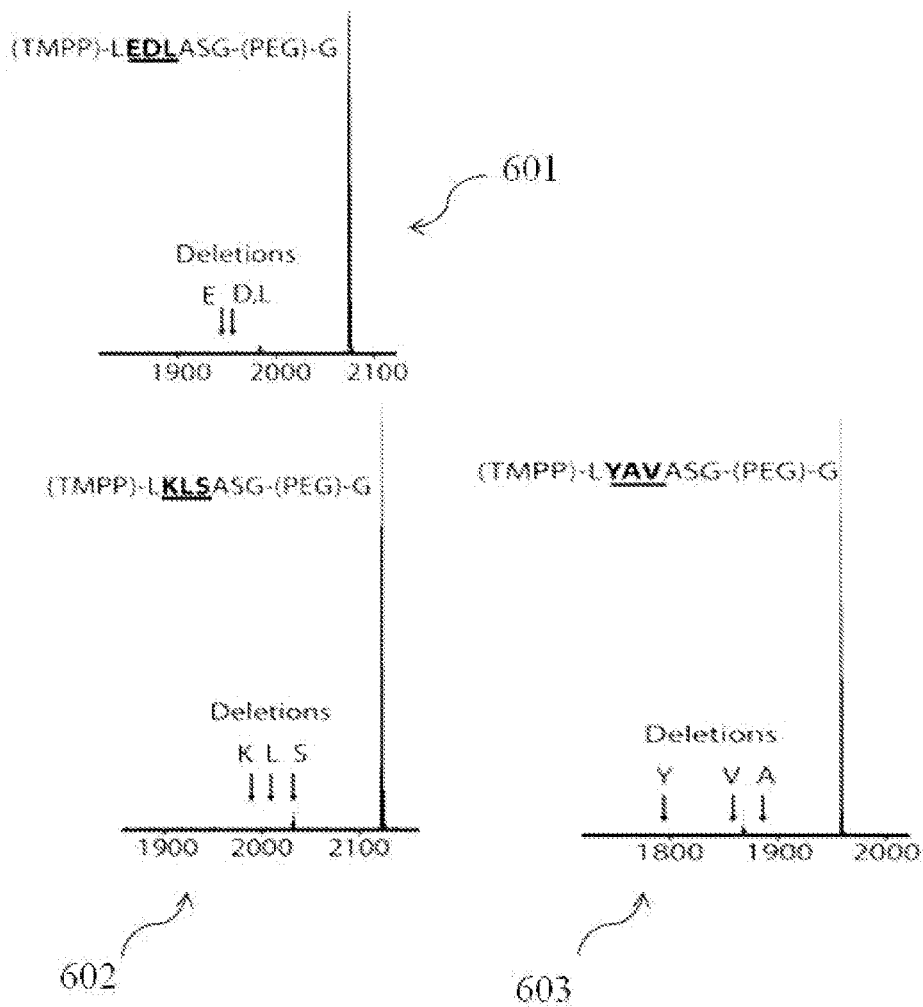
FIG. 6 is a graphic representation of a MALDI spectra of short peptides that differ only in three amino acids.

FIG. 5 shows mass spectra of several peptides made with 23 coupling steps, showing that long sequences can effectively be generated. MALDI mass spectra from individual 200 micron features in which peptides containing 21 amino acids plus a tris(2,4,6trimethoxyphenyl)phosphonium-acetyl (TMPP-Ac) group and a 30 atom polyethylene glycol linker were synthesized, each panel in FIG. 5, 501, 502, 503, corresponds to a MALDI mass spectra from a different long sequence. FIG. 6 shows a series of spectra from shorter peptides that differed from each other in only three amino acids. 601 corresponds to a MALDI spectra of a shorter peptide with E, D, and L amino acid deletions. 602 corresponds to a MALDI spectra of a shorter peptide with K, L, and S amino acid deletions. 603 corresponds to a MALDI spectra of a shorter peptide with Y, V, and A amino acid deletions. Coupling yields of the three variable amino acids were estimated by comparing the ion intensity of the full length peak with the ion intensity observed at the positions expected for each possible amino acid deletion (see arrows). The stepwise yield is shown in TABLE 1 for each amino acid represent the average of results from multiple peptides. The average yields are at or above those achieved by bead-based peptide synthesis. The results indicate that the fabricated in situ synthesized peptides are synthesized in high yield.

TABLE 1

| | |
|---|---|
| A | Greater than 99% |
| V | Greater than 99% |
| P | Greater than 99% |
| L | Greater than 99% |
| G | Greater than 99% |
| Y | Greater than 99% |

TABLE 1-continued

| | |
|---|---|
| F | Greater than 99% |
| S | Greater than 99% |
| N | Greater than 99% |
| Q | 99% |
| K | 97% |
| R | 99% |
| D | Greater than 99% |
| E | Greater than 99% |
| H | Not available |
| W | Not available |

In some embodiments, the processes and methods disclosed herein can be done entirely or primarily using electronics fabrication instruments that have been developed for the electronics industry. In some embodiments, no special chemicals, special flow cells, no off-track processing (other than the initial cleaning and surface preparation) are used, which may lead to very fast cycle times (about 15 minutes per cycle), a key issue when processes involve 100-300 cycles typically.

In some embodiments, the processes and methods for in situ synthesizes of a chemical library are used to fabricate higher density arrays (660,000 features per cm$^2$), which can be critical for applications, such as clinical testing, that require many identical arrays for training and testing. For example, in the case of a diagnostic peptide array assay, if one was to run a trial using 10,000 peptides in triplicate, it would be possible to run many thousands of assays (enough for an entire trial) using arrays from a single wafer. In some embodiments, the processes and methods for in situ synthesis of a chemical library described herein are used in conjunction with methods of health monitoring.

In addition, while one could use a number of substrates with this approach, including glass, the approaches disclosed herein can be compatible with wafers that have been pre-processed to have electronic components. The potential for precise patterning of in situ synthesized chemical systems on electronic components (with the same spatial precision and alignment capability as the original electronic fabrication) lends itself to many research and application possibilities in hybrid electronic systems that are not available with most other array synthesis approaches. In some embodiments, the methods and devices disclosed herein can be expanded to provide other structural motifs, chemical bonds or monomer types, including phosphodiester bonds, amide bonds, ester bonds, thioester bonds, ether bonds, carbon-carbon bonds, and the like an in situ synthesized chemical library.

Figure 7:
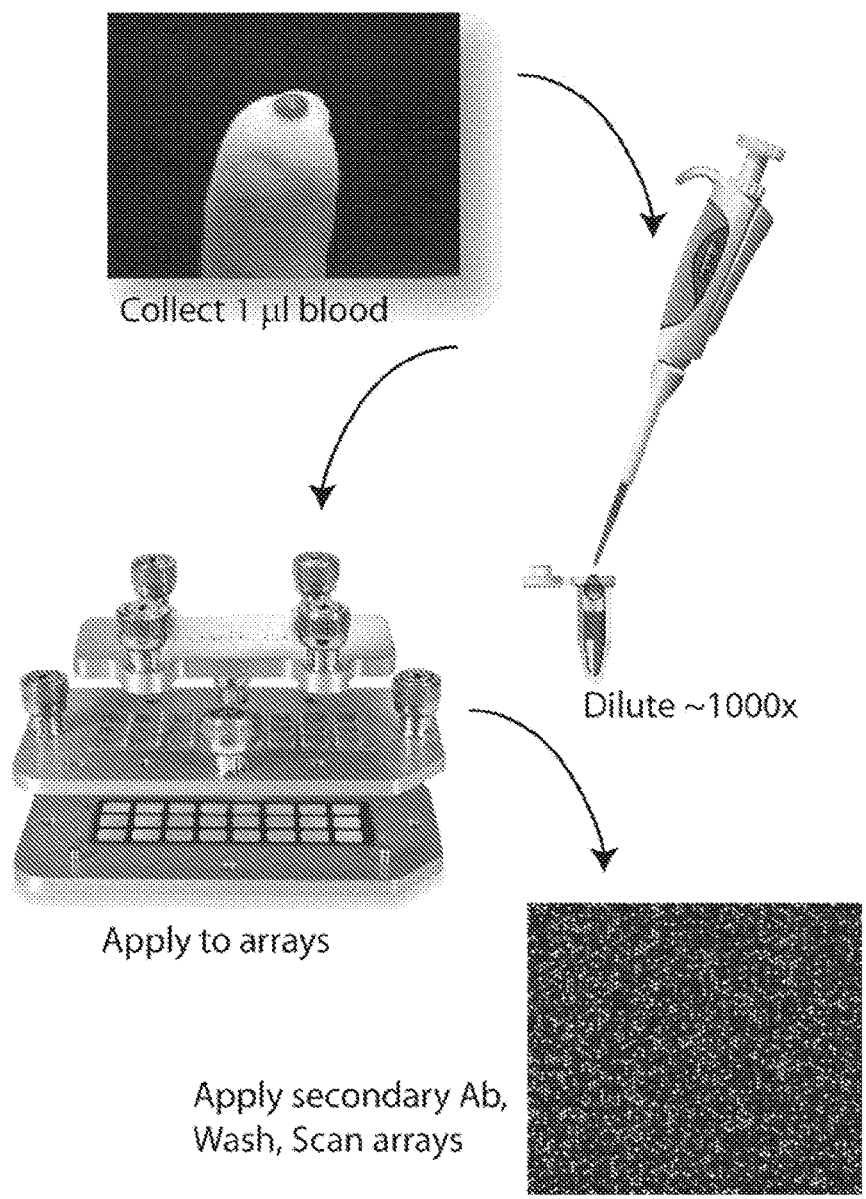
FIG. 7 illustrates an Immunosignaturing process consisting of drawing less than a microliter of blood, diluting it 500-5000 fold, applying it to an array, applying a labeled secondary antibody (e.g., for IgG or IgA) washing, and reading the array on an array reader. No sample processing is required and the blood sample can be dried on a filter paper and submitted through the mail.

Example 2: Detection of Changes in Health Status and Source of any Infection Using Peptide Array Chips Also disclosed herein are in situ synthesized chemical libraries processed to detect and monitor infectious diseases of a plurality of subjects, including, for example, hospital patients, soldiers in the field or veterinary patients. A subject can be a human, a guinea pig, a dog, a cat, a horse, a mouse, a rabbit, and various other animals. A subject can be of any age, for example, a subject can be an infant, a toddler, a child, a pre-adolescent, an adolescent, an adult, or an elderly individual. An immunosignature can be a profile of the circulating antibodies in the blood, determined by taking a small volume of a biological sample, for example, a fraction of a microliter of blood, diluting it, and allowing the antibodies to bind to a set of many thousands of peptides in an array on a surface, such as an in situ synthesized chemical library of the invention (FIG. 7) (Hughes A K, Cichacz Z, Scheck A, Coons S W, Johnston S A, Stafford P. Immunosignaturing can detect products from molecular markers in brain cancer. *PloS one.* 2012; 7(7):e40201; Restrepo L, Stafford P, Magee D M, Johnston S A. Application of immunosignatures to the assessment of alzheimer's disease. *Ann Neurol.* 2011; 70(2):286-295; and Legutki J B, Magee D M, Stafford P, Johnston S A. A general method for characterization of humoral immunity induced by a vaccine or infection. *Vaccine.* 2010; 28(28): 4529-4537).

A plurality of biological samples can be analyzed with an in situ synthesized chemical library and methods of the invention for the detection of changes in health status and identification of infections. In some embodiments, the biological sample that is contacted with an in situ synthesized chemical library comprises, blood, serum, saliva, sweat, cells, tissues, or any bodily fluid. In some embodiments no more than about 0.5 nl to about 50 nl, no more than about 1 nl to about 100 nl, no more than about 1 nl to about 150 nl, no more than about 1 nl to about 200 nl, no more than about 1 nl to about 250 nl, no more than about 1 nl to about 300 nl, no more than about 1 nl to about 350 nl, no more than about 1 nl to about 400 nl, no more than about 1 to about 450 nl, no more than about 5 nl to about 500 nl, no more than about 5 nl to about 550 nl, no more than about 5 nl to about 600 nl, no more than about 5 nl to about 650 nl, no more than about 5 nl to about 700 nl, no more than about 5 nl to about 750 nl, no more than about 5 nl to about 800 nl, no more than about 5 nl to about 850 nl, no more than about 5 nl to about 900 nl, no more than about 5 nl to about 950 nl, no more than about 5 nl to about 1 µl no more than about 0.5 µl to about 1 µl no more than about 0.5 µl to about 5 µl, no more than about 1 µl to about 10 µl, no more than about 1 µl to about 20 µl, no more than about 1 µl to about 30 µl, no more than about 1 µl to about 40 µl, or no more than about 1 µl to about 50 µl of biological samples are required for analysis by an in situ synthesized chemical library and method of the invention.

An in situ synthesized chemical library of the invention can detect a very small concentration of target in a sample, and thus requires very little sample for detection. In some embodiments, a dilution of a sample can provide an optimum concentration of an antibody from a biological sample of a subject for characterization by an in situ synthesized chemical library of the invention. In some embodiments, the samples are diluted at least by 2-fold, by 3-fold, by 5-fold, by 10-fold, by 20-fold, by 30-fold, by 40-fold, by 50-fold, by 75-fold, by 100-fold, by 250-fold, by 500 fold, by 750-fold or at least by 1000-fold.

Different antibodies bind to different peptides so as to create a disease-specific "signature". The objective with regards to the use of an in situ synthesized chemical library and a method of the invention can be to combine the discovery and intelligent processing of a pattern of antibodies from a sample of a subject with a stable, scalable manufacturing platform for peptide arrays based on standard electronic fabrication instrumentation. With such a system it can be possible to detect any disturbance in the health of a subject, for example, a human subject serving in the military, that is reflected in the antibody profile of the subject. This can include early signs of infection, even by yet unknown bioagents. Also included herein are in situ synthesized chemical libraries and methods allowing near real-time readout of a health status of a subject.

Figure 8:
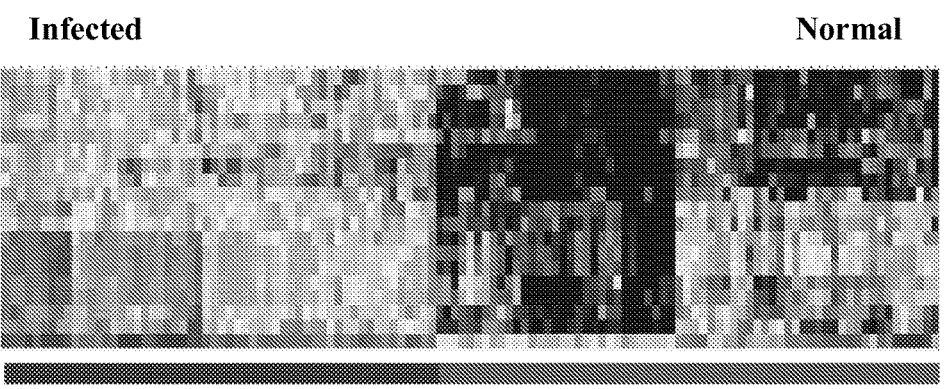
FIG. 8 is a heat map comparing an Immunosignaturing profile of subjects infected with valley fever (Coccidiomycosis) and subjects not infected with valley fever. Each column is a patient (approximately 90 infected and 90 normal), and the rows are the ~100 peptides selected as informative for the disease. The color indicates the level of binding of IgG to each peptide (red=strong, blue=weak).

An example of detecting a health status of a subject with the in situ synthesized chemical libraries and methods described herein is the detection of an infectious fungal disease (valley fever, coccidiomycosis) as shown in FIG. 8. Blood was collected from ~200 patients who entered the Valley Fever clinic at the University of Arizona FIG. 8. Of these, 120 turned out to be infected with the Valley Fever and the remainder were not infected or were infected with a different disease. This was used as a training set. An independent, blinded set of blood samples from 180 patients (about half normal, half infected) were collected. In this case, the blood from infected patients was collected at a time before the standard immunological test was positive (zero-titer samples). FIG. 8 illustrates a heat map displaying the intensity of fluorescence (IgG binding) to a subset of informative peptides on a peptide array with 10,000 peptides. Each column is a different sample. As can be seen, the samples were identified with 100% specificity and 100% sensitivity. The experiment described above was performed with 10,000 feature printed peptide arrays, and can be performed, for example on 330,000 feature in situ synthesized peptide arrays.

TABLE 2 gives a comparison of the performance between printed arrays and in situ synthesized arrays in distinguishing between individuals before and after receiving the 2006 influenza vaccine. This particular vaccine was chosen because it gives a rather subtle immune response in contrast to the immune response typically generated in response to an infection with valley fever. Blood samples were taken from 5 individuals before and after vaccination. For both the printed and in situ synthesized arrays, 2 technical replicates were run on each individual sample. Data from pre- and post-vaccination were then compared using a standard, 2-tailed t-test and the number of statistically significant peptides (the number of peptides with p-values less than the inverse of the number of peptide features) was determined. In addition, the number of peptides which showed a 2-fold change between pre- and post-vaccination was also determined.

The distinctions between printed arrays and in situ synthesized arrays are tabulated in TABLE 2. The data of TABLE 2 suggests that the in situ synthesized arrays can be about 10-fold more sensitive than the printed arrays. This is significant in terms of how early an infection can be detected.

TABLE 2

| Type of Array | Number of Features | Serum Dilution | Number of Peptides Statistically Different | % Peptides Statistically Different | Number of Peptides greater than 2 fold difference |
|---|---|---|---|---|---|
| Printed arrays | 10,000 | 500–fold | 20 | 0.2% | 0 |
| In situ synthesized arrays | 330,000 | 5000–fold | 18,275 | 5.5% | 11,176 |
| Fold difference between arrays | 33 | 10 | 914 | 27.5 | ∞ |

The in situ synthesized chemical libraries, arrays, methods, and processes described herein can be applied to:
  Exploring reusable or more robust arrays made with non-natural amino acids that will not digest in the presence of proteases;
  Exploring the utility of branched or scaffolded peptide structures to enhance specificity of binding (e.g., taking advantage of both arms of the antibody structure by placing two identical peptides on a branched structure or scaffold the right distance apart);
  Exploring arrays with non-random sequences that have been "evolved" by analyzing random arrays and developing rules for sequences that better distinguish multiple classes of infectious diseases (this could result in much smaller arrays and therefore many more per wafer); and
  Exploring the seamless integration of high density immunosignaturing array generation with sensor architectures. Also incorporated herein is the creation of a fieldable unit for immunosignaturing that utilizes electrochemical luminescence and a fixed photodiode sensor (Zhang L, Tsow F, Forzani E, Tao N. Reversible oxygen gas sensor based on electrochemiluminescence. *Chemical Communications.* 2010; 46(19):3333-3335).

Such technologies can make possible to build an in situ synthesized chemical library directly onto solid state opto-electronic systems (e.g. plasmonic-based electrical impedance imaging approaches, Shan X, Patel U, Wang S, Iglesias R, Tao N. Imaging local electrochemical current via surface plasmon resonance. *Science.* 2010; 327(5971):1363-1366), MEMS systems, conduction based sensors, or electrochemical sensors at high density to create label-free chips for detection with the full complement of peptide features.

Biomimetic Systems.

Also disclosed herein are methods and devices to create peptide ligands that can be "added on" to cellular proteins (either genetically or via external introduction) to change their targeting/sequestration in cells. These new targeting minidomains can be added either to existing or transgenic cellular proteins in a synthetic biology system. The targeting peptides will be selected via binding of the target to large ordered peptide arrays.

In another aspect, disclosed herein are methods and devices to design, synthesize and analyze large ordered libraries of non-natural heteropolymers. While biology has done an adequate job of exploring the space defined by linear heteropolymers of amino acids and nucleic acids, there is very little known about the function space defined by nonlinear heteropolymers and heteropolymers made from either non-natural amino acids and nucleic acids or using alternative monomers and coupling strategies. Using the chemical patterning systems disclosed herein, there is no limitation to natural amino acids, nucleic acids or even to the kinds of linkages involved in those biopolymers. Because millions of such compounds can be made with relatively large numbers of synthetic steps, one method contemplated is to systematically explore the functional attributes of different chemical spaces, combining chemical computation, library synthesis, imaging mass spectrometry and dynamic optical spectroscopy on surfaces. Of particular interest is the development of catalytic activity, specific types of chemical reactivity, molecular recognition, and environmentally-induced molecular responses for use in the methods disclosed herein.

Also disclosed herein are methods and devices to design and create complex interfaces between chemical or cellular systems and electronic systems. Wafers on which electronic components have been patterned can be directly aligned and used to create patterned chemical systems (e.g., sensor molecules) with essentially the same resolution as the electronic component fabrication. A key question is how to use such hybrid systems to transfer information in and out of complex chemical and biological systems: organizing individual cells on surfaces, reading immunosignatures (see above) electronically rather than optically (current approach), and developing molecules that change molecular recognition properties in the presence of electric fields at surfaces.

The Human Pathogen Proteome.

Also disclosed herein are methods and devices to make large quantities of peptides in an ordered array to cover the proteomes of all the known and sequenced human pathogens on a single chip within an area of a few square centimeters. A method for detecting a known proteome on an array can comprise generating a few million overlapping peptides of about 15 amino acids in length that including known and unannotated protein sequences found in the genomes of these organisms.

To test a method of detecting a known proteome with an in situ synthesized chemical library preliminary studies have been performed looking at the binding of serum antigens from individuals infected and non-infected with viruses to arrays of 5,000 peptides that partially represent the proteins from 19 pathogens. Four diseases/vaccines were studied (West Nile virus, tularemia, valley fever and small pox vaccine). For the four diseases studied antigens from the proper organism gave rise to an immune response on a human subject that allowed an accurately identification of infection by that pathogen.

In some embodiments, the in situ synthesized chemical library of the invention can comprise features corresponding to pathogenic epitopes, a "pathogenic array". An in situ synthesized chemical library comprising pathogenic epitopes can be used in, for example:

The identification of a broad range of infectious agents from symptomatic patients, pre-symptomatic patients, and/or asymptomatic patients;

Determining if vaccination for a specific disease agent is effective; and

"Unmasking" infectious agents potentially involved in chronic conditions such as Gulf War Syndrome using historical samples.

Rapid Development of New Antimicrobials.

Also disclosed herein are methods and processes used in the development of antimicrobial therapies. An in situ synthesized chemical library can be applied to the rapid discovery of a set of ligands, and an in situ synthesized chemical library can provide a method for combining a discovered ligand and an effector molecule into a multivalent targeted drug. This process can be similar to previously developed technology for the generation of synthetic antibodies (Synbodies, Williams B A R, Diehnelt C W, Belcher P, et al. Creating protein affinity reagents by combining peptide ligands on synthetic DNA scaffolds. *J Am Chem Soc.* 2009; 131(47):17233-17241; Gupta N, Belcher P E, Johnston S A, Diehnelt C W. Engineering a synthetic ligand for tumor necrosis Factor—Alpha. *Bioconjug Chem.* 2011; 22(8):1473-1478). Direct binding of fluorescently labeled bacteria or viruses to peptide arrays and screen for specific ligands can be used in the assembly of the antimicrobial was demonstrated using the methods and devices disclosed herein. The resulting antimicrobials were effective in vitro at concentrations that did not result in significant hemolysis. In order to develop drugs suitable for in vivo use, it will be necessary to increase the lifetime of the drug candidates in the body before clearance or degradation. The ability to use a large variety of non-natural amino acids and branched structures in arrays created with the proposed instrumentation would be of tremendous benefit. In addition, the large number of peptides or peptide-like molecules available in the arrays will allow selection of higher affinity ligands with the desired specificity.

An exemplary embodiment of the cluster system used consists of a model P9000 cluster unit from C & D Semiconductor integrated with a model 5008A proximity/contact mask alignment and exposure system from Optical Associates, Inc.

Cluster Systems and Devices.

A P900 cluster system from C&D Semiconductor Services, Inc., can be a primary robotic unit for the fabrication of an in situ synthesized chemical library. It can have modules for spinning coating, reaction chambers, heat blocks and cooling blocks, as well as a robotic arm that places wafers in different modules as programmed.

A model A 5008A proximity contact mask alignment and exposure system from Optical Associates, Inc., can be integrated into the cluster unit. It can picks up the wafer from a staging area using its own robotic arm and places the wafer appropriately for mask alignment and UV exposure.

These two units can allow to robotically run the fabrication of patterned chemical syntheses with many steps on 6 or 8 inch wafers, within a controlled (particles, temperature and humidity) environment. In some embodiments, the characteristics of a cluster system and devices can include:

Single, programmable interface;

Modules for spin coating, heating, cooling and alignment/exposure all accessible to a programmable robotic system;

Two of the heating modules will be capable of "vapor priming", making it possible to avoid evaporation from the surface during the heating cycle associated with chemical reactions (these will be the chemical reaction chambers for coupling);

1:1 contact or proximity alignment and exposure meaning that the entire surface of the wafer can be uniquely patterned;

Alignments within 1 micron;

Minimum feature size approximately 5 microns;

1000 W lamp with filters restricting the wavelength range to a narrow region near 365 nm (I-line);

For most processes, up to 4 wafers can be processed simultaneously;

Enclosed environment controlled for particle count, temperature and humidity;

Manual loading of syringes with different amino acids (one syringe for each step of the process) and masks (manually loaded, but auto-aligned); and For standard processes, modeling of the system has indicated cycle times of about 15 minutes (assuming 4 wafers cycled simultaneously).

System Configuration.

Figure 9:
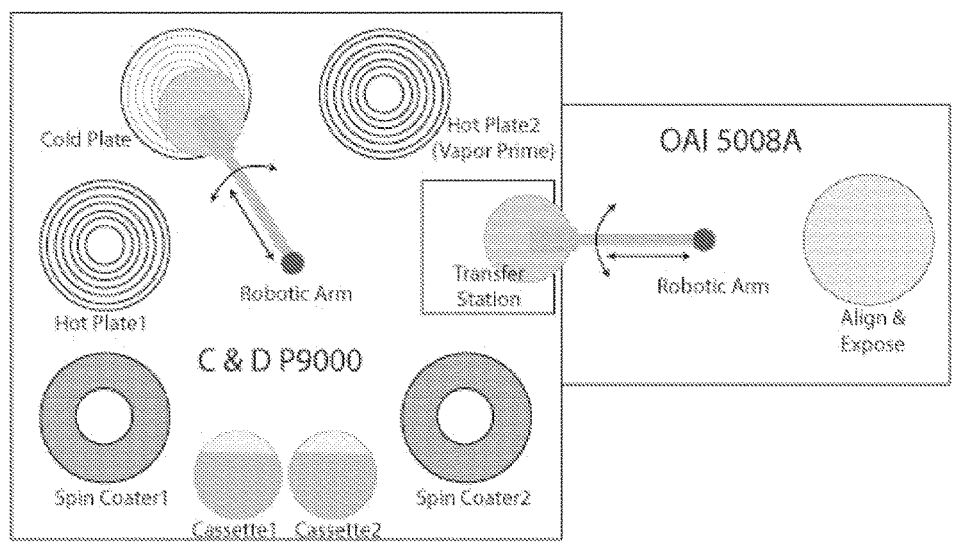
FIG. 9 is a diagram of an instrument configuration.

An overview of an exemplary configuration of a cluster system for the generation of an in situ synthesized chemical library is given in FIG. 9. In the P9000 cluster unit, spin coater 1 can be used for delivering and removing photoresist including back-side washing and edge-bead removal. Spin coater 2 can be used for applying and removing the chemical coupling solutions, again including back-side washing. Hot plate stack 1 (3 stacked hot plates) can be used for pre- and post-bake associated with the photoresist. Hot plate stack 2 (2 stacked vapor prime modules) can be used for performing chemical reactions with thin films of solvent (typically low vapor pressure liquids such as dimethylformamide or N-methylpyrrolidone) on the surface. The vapor prime modules can be closed when in use, filled with solvent vapor and contain a hot plate that rapidly brings the wafer to the proper temperature for the reaction. The cold plate can rapidly and uniformly bring the wafer to ambient temperature after heating. There are two cassette holders for adding wafers, leaving wafers in parking states and collecting finished wafers. The robotic arm of the P9000 unit can control the programmed movement of up to four wafers as they simultaneously pass through the process cycle. The final station of the P9000 cluster unit can be a transfer station. This can be effectively a cold plate where wafers are parked waiting to be transferred into an aligner, such as the OAI model 5008A aligner. There can be a separate robotic arm in this unit that then picks up the wafer and transfers it to the align/expose unit which aligns the wafer relative to etched or deposited alignment marks and exposes with 365 nm light for a programmable time from a 1000 W lamp through an auto-aligned, 1:1 mask set either for contact or proximity patterning.

Example 3: Evaluating the Synthesized Arrays

It is possible to start the process using a probability less than N/M and then increase the probability during the synthesis to avoid the initial sequence bias described above. The algorithm described above was applied to the theoretical (in silico) production of an array of 10,000 peptides. The number of monomers used was 16 (R=16) and the length of each peptide was 17 (N=17). The total number of steps used in the theoretical in situ patterned synthesis was set at four different values for comparison, M=35, M=70, M=140 and M=272 (note that R×N=272). The relative randomness of these peptides was evaluated in a number of ways. One simple way to consider randomness is to look at the distribution of how each mask (and each mask is associated with an amino acid) contributes to particular positions in the 17-long peptide sequence.

Figure 10:
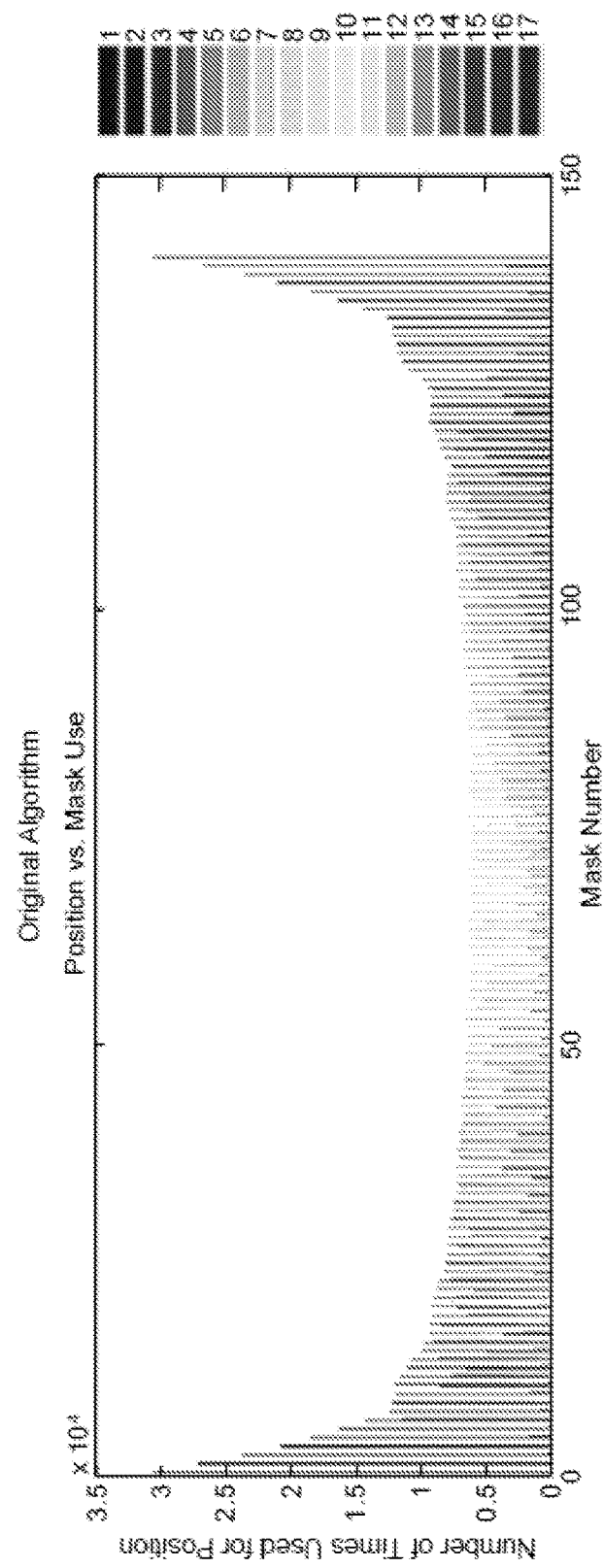
FIG. 10 is a plot of randomness distribution of 17-mer peptides using M=140 masks for peptide synthesis.
Figure 10:
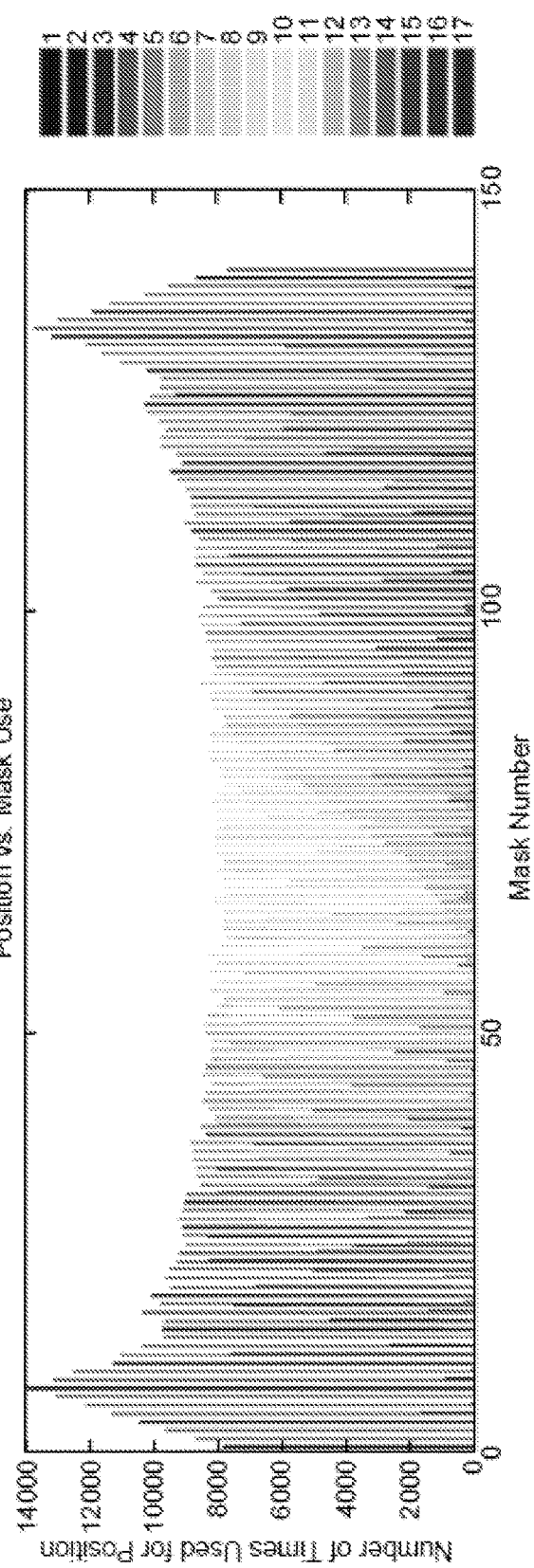

FIG. 10 shows a plot for M=140. The top panel shows the result if the algorithm described above is applied in an unmodified form. The different positions in the peptide (the 17 residues) are colored such that blue is near the beginning of the peptide and red is near the end. Note that there is a bias in the frequency of use of some of the early masks in the first few positions, resulting in a nonrandom amino acid incorporation in those positions. This can be corrected by decreasing the frequency of use of the initial few masks (decreasing the number of features exposed by those masks). The result of one such bias correction is shown in the lower panel of the figure. All of the different theoretical sets described below were modified in this way (M=35, 70, 140 and 272).

One can also evaluate randomness of sequence by asking how many unique sequences of 2, 3, 4, etc. amino acids there are in the peptide population. This was done for limiting groups of 384 peptides for each number of steps. One would expect that in a truly random system, essentially all possible amino acid dimers would be represented in 384 peptides of length 17 (256 if 16 amino acids are used). Most possible trimers would also represented (4096). A statistical representation of longer sub-sequences would also be represented.

Figure 11:
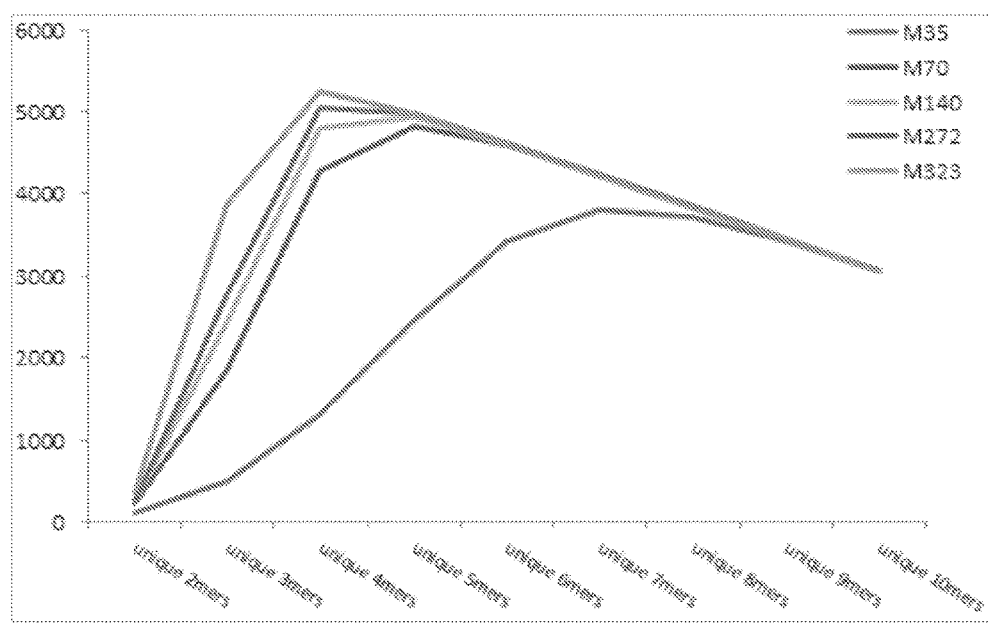
FIG. 11 is a graph illustrating the distribution of unique peptides with varying mask configurations.
Figure 12A:
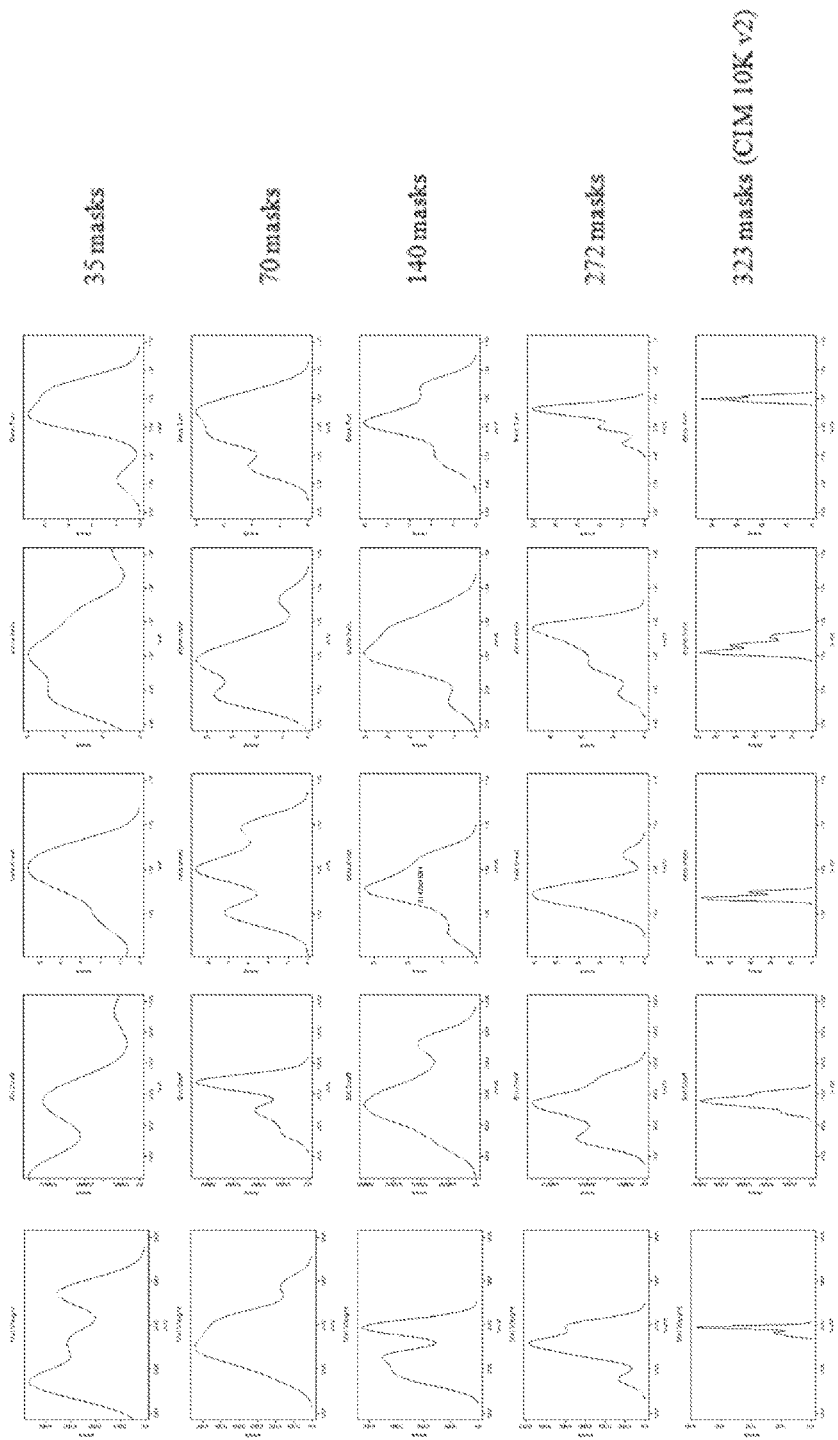
FIGS. 12A-C are graphs illustrating the distribution of peptides with varying mask configurations.
Figure 12B:
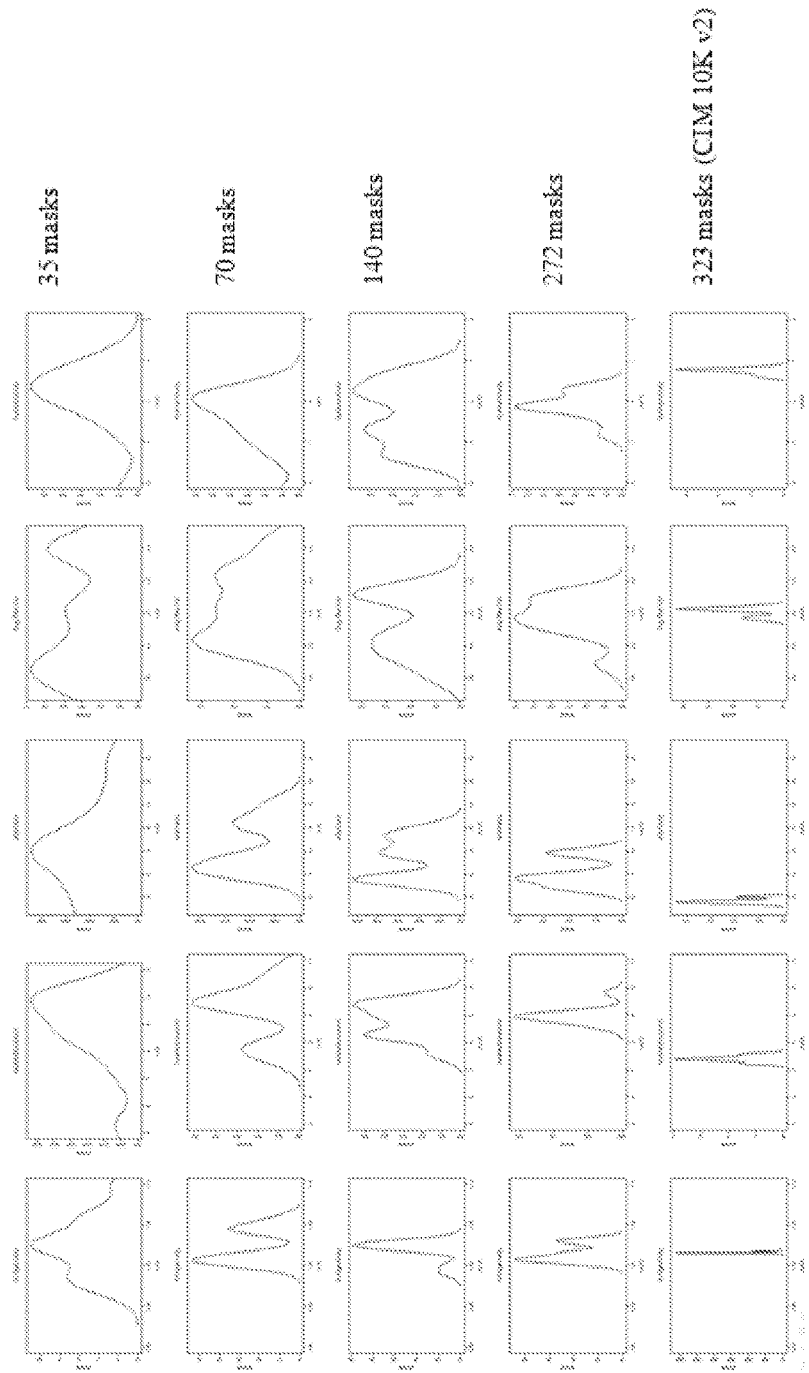
Figure 12C:
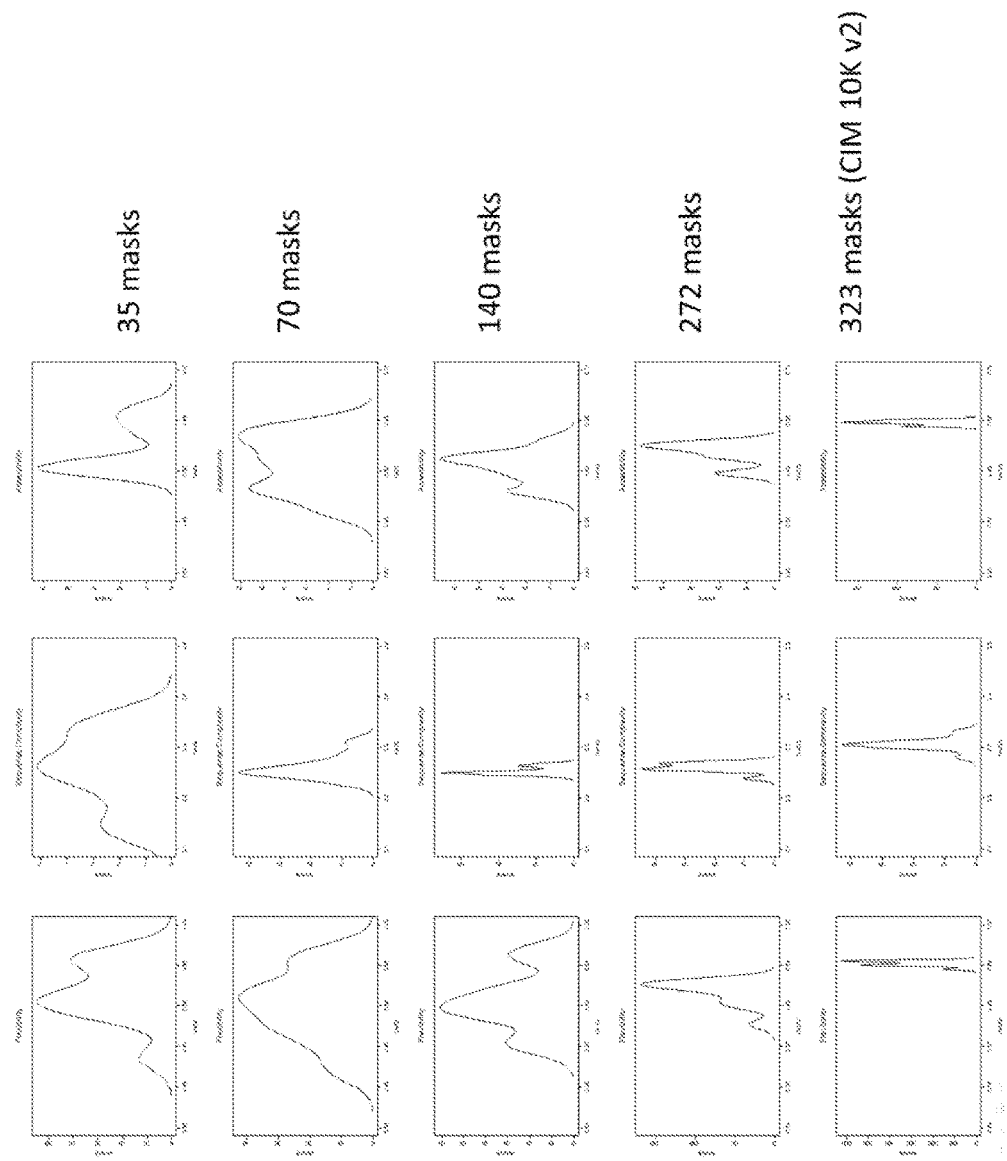

As can be seen in FIG. 11, the distribution is most random (must unique n-mers) for the larger number of steps, but the values for M=272 and M=140 are very similar, M=70 a bit lower and M=35 is very different. M=35 results in only a relatively constrained exploration of sequence space. One can also look at the predicted distribution of physical parameters associated with the peptides created as well. FIG. 12 provides a series of plots of different characteristics of each peptide including (in order from left to right): Molecular Weight (from 2.2 to 3 kD), Extinction coefficient (from 3000 to 14,000), beta sheet tendency (from 0.9 to 1.15), Alpha helix tendency (from 0.95 to 1.06), Beta turn tendency (from 0.80 to 1.10), Antigenicity (from 0.90 to 1.10), Isoelectric point (from 5 to 12), Aliphatic character (from 10 to 22), Average residue volume (from 3.5 to 4.5), Hydrophilicity (from −2 to 2), Flexibility (from 0.95 to 1), Sequence complexity (from 2.1 to 2.5), Accessibility (from 0.50 to 0.70). Data was obtained from ExPASy's ProtParam tool (expasy.org/protparam). Rows indicate the mask numbers used to create the 100,000 peptides using for this analysis, from M=35 (top) to M=272 (bottom). As seen in FIG. 12, as the number of steps increases, the width of parameter distributions decrease. This is because truly random sequences of 17 amino acids have more similar physical parameters on average, while less random sets of sequences contain a larger number of statistical outliers.

384 actual peptides from each of the simulations (M=35, M=70, M=140, M=272) were then synthesized using conventional bead-based synthesis at 80% purity and printed onto a surface in an array format. Each of these types of arrays was then tested against 105 different monoclonal antibodies. The question asked was whether higher randomness resulted in greater ability to distinguish between monoclonal antibody binding. Note that the 384 peptides made using the algorithm for each M value did not contain the cognate sequence for any of the antibodies. However past work has shown that monoclonal antibodies bind to roughly 2% of random peptide sequence to some extent and that given enough diversity, different monoclonal antibodies show distinctly different binding patterns.

TABLE 3

|  | Correlation averages (antibodies) |
| --- | --- |
| M = 35 | 0.6843 |
| M = 70 | 0.6470 |
| M = 140 | 0.5015 |
| M = 272 | 0.3057 |

The correlation shown is the average correlation between the patterns generated using different monoclonal antibodies. Note that the correlation between technical replicates (the same antibody) was greater than 0.90. Thus, one would expect that different antibodies would give different patterns and therefore a much lower correlation than technical replicates. As the number of steps increases, the correlation drops, indicating that a more random peptide distribution can more easily distinguish between the binding of different monoclonal antibodies.

Thus, using the algorithm described above, one can substantially decrease the number of steps involve in the synthesis of pseudo-random in situ synthesized patterned chemical libraries on a surface. Although there is a decrease in the degree of randomness when one decreases the number of synthesis steps, determined as described above, for many applications this decrease is acceptable given the substantial drop in cost and time associated with fabricating the array. It is also the case that one can often make a larger array (use more area on the surface or make the features smaller) to compensate for loss in randomness (obtain better coverage of the possible sequence space through larger numbers of sequences represented). Information content increases roughly linearly with the number of features (number of different peptides) made, because the total possible space of peptide sequences is extremely large compared to the number of features that realistically can be fabricated on a surface. Thus it is possible to effectively trade space for manufacturing time and total cost per manufacturing run by applying the approach described above to decrease the number of fabrication steps, while adjusting the total number of peptide features.

Example 4: An In Situ Synthesized Chemical Library from Thin Layers of Reaction Mixtures on Surfaces Also disclosed herein are methods and devices for chemical coupling from thin layers of reaction mixtures on surfaces. It has become possible to create relatively large chemical libraries through in situ synthesis on solid surfaces forming patterns of synthetic molecules on said surfaces. Types of chemical libraries currently made and sold commercially in this way include oligonucleotide libraries and peptide libraries. Commercial vendors of such in situ synthesized libraries include Nimblegen-Roche™, Affymetrix™, Agilent™, and LC Sciences™.

Other types of chemical libraries could be made using similar methods including peptoid libraries, peptide nucleic acid (PNA) libraries and other patterned chemical libraries on surfaces. The libraries do not have to be restricted to phosphodiester or amide bonds. Ester bonds, thioester bonds, ether bonds, carbon-carbon bonds are examples of other bonds that could be formed and many types of chemistry can be used to create these bonds, as has been demonstrated in general for solid phase synthesis and is well known to those in the art.

The libraries synthesized in these ways do not have to be restricted to linear structures. Branched structures have been demonstrated and it is possible to add groups to an existing molecular scaffold as well. The monomer molecules used to make these in situ synthesized patterned chemical arrays do not have to be natural amino acids or nucleic acids. In fact they can be of a very broad range of chemical types. It is even possible to make patterned chemicals on surfaces using monomer molecules of different types and with different bonding connections. Patterning can be done using any of a large number of methods including photolithography acting on photolabile groups or photolithography acting on molecules that produce acid or base, or the use of electrodes to oxidize or reduce compounds or direct printing of chemicals onto surfaces containing the reactive compounds, or any of a number of other means of patterning compounds on a surface in such a way that they react to form new molecular species. It would be advantageous to perform all of the processes involved in a patterned chemical reaction sequence directly using standard fabrication equipment common to the semiconductor manufacturing industry.

Here methods are described for running chemical coupling reactions based on reaction mixes that are spun onto surfaces on a spin-coater and then heated using commercially available heating modules for electronic fabrication equipment. The primary advantages of performing the reactions in this way, as opposed to, for example, batch chemistry off of the track, are two-fold: reduced cycle times and reduced volumes of chemical coupling materials.

Consider a surface that has affixed to it one or more chemically reactive groups in a pattern. That pattern of chemically reactive groups can be generated in a number of ways, such as those used in the in situ DNA or peptide array synthesis field (see some of the companies listed above). Once that pattern is created, it is often desirable to react the pattern of chemically reactive groups with a reaction mix that modifies the surface where ever the chemically reactive groups are exposed. An example would be adding an amino acid to a growing peptide chain only in those features on the surface where the protective group has been removed from the N-terminal amine of the peptide.

Here two methods are described for spin-coating a thin layer of reaction mix on the surface and heating it in such a way that the reaction occurs rapidly and evenly. The primary issues involved are the evaporation of the thin film of solvent containing the reactants before the reaction is complete and maintenance of a complete coating of the chemical reaction mix across the surface.

Method 1: The reaction mix is spun onto the surface at ambient temperature (or a temperature where the solvent will not instantly evaporate) and a second wafer is placed on top of the first, creating a sandwich in which the thin liquid layer is trapped between the two wafers and cannot either evaporate or redistribute. This can be done directly with simply a second bare wafer, or the second wafer can have small pins or a thin gasket which hold it off of the first wafer just enough (up to several hundred microns) to make separation at the end of the reaction easier. After the liquid is trapped between the wafers, the whole assembly is heated on a standard hot plat at the desired temperature for the desired time.

Figure 13:
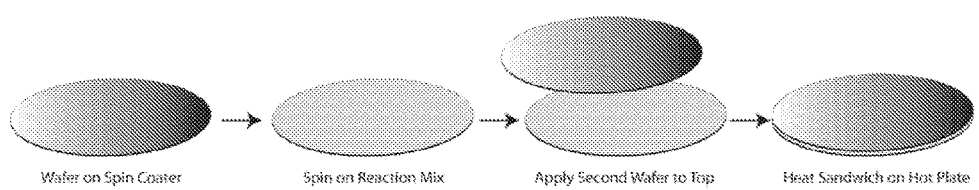
FIG. 13 is a schematic of in situ peptide synthesis.

The process is shown schematically in FIG. 13. The potential disadvantage with method 1 is that the separation of the two wafers after the reaction can be difficult, depending on the nature of the reaction coupling mix in between. This is particularly an issue when automating the process.

Method 2: The second method involves employing a vapor prime module with a heat block as the reaction chamber. In this case, the reaction mix is spun onto the wafer as in method 1, but instead of applying a second wafer to the top, the wafer with the reaction mix is placed onto a hot plate in a chamber. The chamber has nitrogen (or some other gas or air) flowing through it which has been bubbled through the solvent used in the chemical reaction mix. As a result, little or no evaporation of the solvent from the surface of the wafer occurs.

Method 1 was used to create a peptide uniformly across the surface of a wafer via a series of coupling reactions such as the one shown above. The following experimental conditions are exemplary of the coupling reactions that may be employed in the in situ synthesis of peptides. Modifications in solvent and reaction components and concentrations can be made in the synthesis of peptides at, for example, the surface of arrays. Moreover, experimental conditions may also be varied, including changes in temperature and incubations times, in order to effectuate in situ peptide synthesis. These variations are contemplated within the parameters of the methods and devices disclosed herein.

Figure 14:
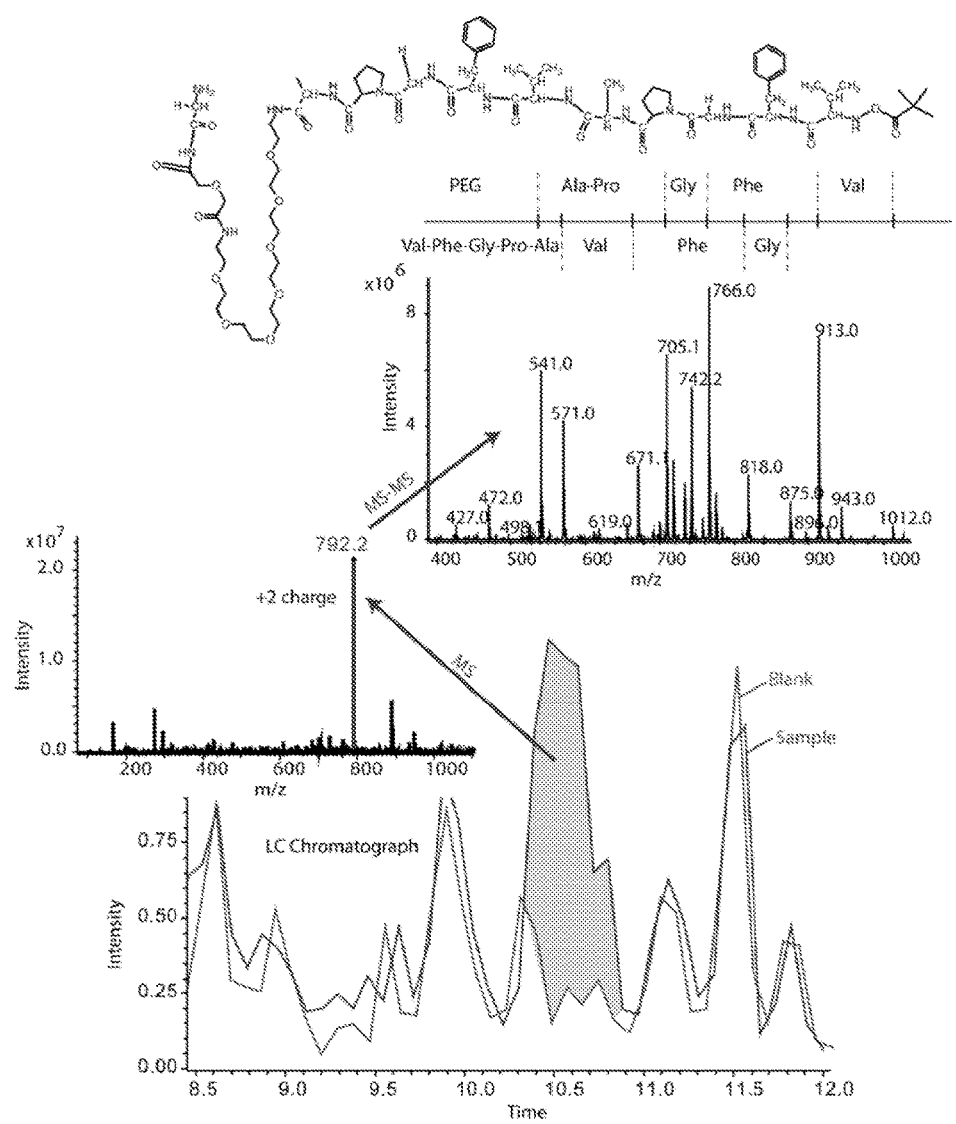
FIG. 14 is an LCMS analysis of in situ peptide synthesis.

The specific coupling reaction was run using 0.1 M amino acid at each step, 0.1M HOBt (Hydroxybenzotriazole) and 0.1 M diisopropylcarbodiimide all in NMP (N-methylpyrrolidone) solvent. This peptide had the sequence PEG-Ala-Pro-Gly-Phe-Val-Ala-Pro-Gly-Phe-Val. It was made on a cleavable linker attached to the surface, cleaved from the surface, concentrated and run through liquid chromatography mass spectrometry (LCMS) analysis. The results are seen in FIG. 14. It was not only possible to detect the full length peptide, but it could be directly sequenced by mass spectrometry. FIG. 14 bottom, chromatogram showing the elution time of the peptide. The other peaks were present in the blank. Mass spectrometry of this peak gave one dominant mass (next spectrum above the chromatogram) which could then be directly sequenced (third spectrum). The structure of the peptide is shown at the top.

It has also been possible to demonstrate this method in patterning features. FIG. 4 shows matrix assisted laser desorption ionization time of flight (MALDI) from several different patterned features on the surface. Each has the molecular mass expected for the peptide made at that feature using the coupling method 1 described above.

Method 2 has been reduced to practice by demonstrating that it is possible to couple an amino acid to the surface (using the same solution as above) and in so doing mask a free amine group. Free amines were then assayed by coupling to carboxy-biotin and incubating with fluorescently labeled streptavidin. Before coupling, a strong signal was observed indicating that amines were present. After labeling, the signal strength was greatly reduced, indicating that the coupling had taken place.

Also disclosed herein are methods and devices for high throughput processing of patterned chemical arrays formed on wafers. As discussed above, it has become possible to create relatively large chemical libraries through in situ synthesis on solid surfaces forming patterns of synthetic molecules on said surfaces.

Methods of in situ synthesis sometimes involve the creation of many small arrays on large surfaces such as silicon wafers. While it is possible to dice the individual arrays, the handling of these arrays and the use in standard systems for handling biological or environmental samples can be difficult. Many biological sample handling and assay processes involve glass slides that are 25×75 mm and 1 mm thick. These slides can then be used in many ways, but one way is to use commercial gaskets that subdivide each slide into subsections for independent analyses. Such gaskets are sold by companies such as ArrayIt. Thus one useful arrangement of patterned chemical arrays on a large surface, is such that the larger surface is be divided into slides and on each slide are designed and configured a set of separate arrays in the correct position to be used with a commercial gasket system. In this way, one can take advantage of existing systems for both incubating patterned chemical arrays with solutions (multiple different solutions and thus multiple assays per slide shaped section) and for reading the slides (there are many different slide readers available commercially, particularly for reading fluorescence). Using 1 mm thick substrates (rather than 0.75 mm substrates that are common in the electronics fabrication industry) greatly facilies the interconvertability.

Figure 15:
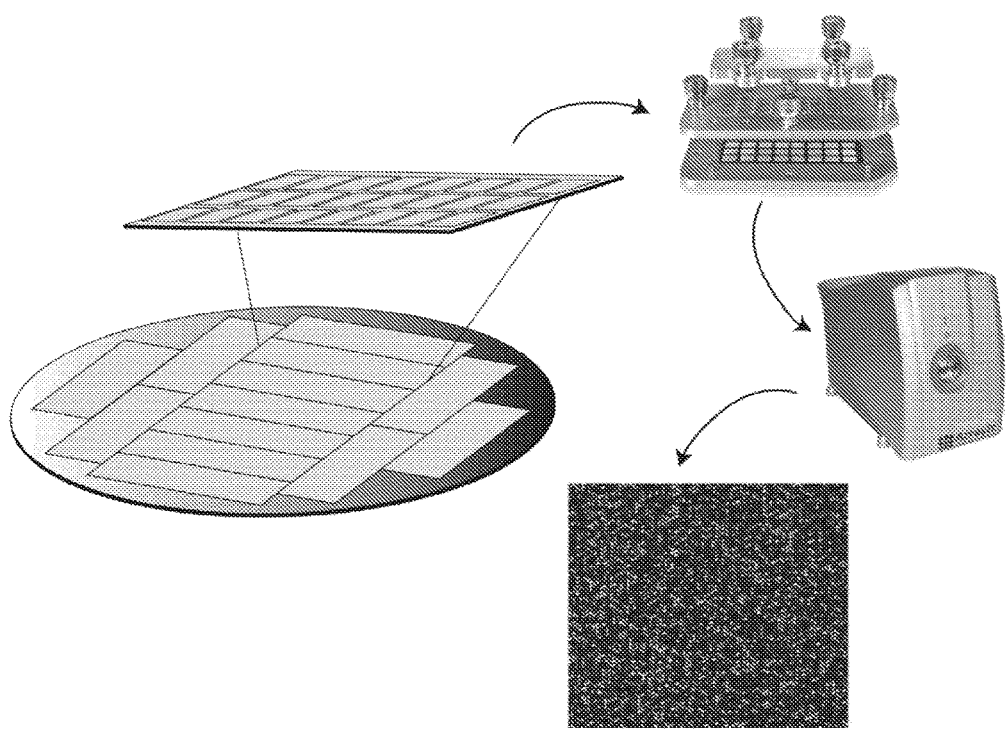
FIG. 15 is an illustration of a wafer design and a fluorescence reading output.

A specific example of such a wafer design is shown in FIG. 15. The following experimental example is exemplary of the experimental conditions reactions that may be employed in the in situ synthesis of peptides on an array, including for example, modification of the number of arrays per slide and feature density. For example, gaskets can be made to change the number of arrays per slide from 2 per slide to 24 arrays per slide. With the changes in array sizes, feature density on an array can also change. Feature density can vary from 330,000 to 1,000,000 features in a 0.5 cm$^2$ area, or 500,000 to 100,000,000 features in a 0.5 cm$^2$ area. These variations are contemplated within the parameters of the methods and devices disclosed herein.

In the case of FIG. 15, in situ patterned synthesis of arrays of 330,000 peptides was performed on a 1 mm thick, 200 mm diameter silicon wafer. Each array is 0.5 cm$^2$ and the arrays on the wafers are organized into groups of 3×8 arrays that fit on a microscope-slide-sized (25×75 mm) section of the wafer. After dicing, the pieces of silicon that result are exactly the same size as microscope slides and can be used with the Arrayit RC1X24 multiplexed microarray hybridization cassette and associated gaskets. This allows one to easily run 24 separate assays simultaneously and then use a commercial fluorescent slide reader to read the results from all 24 assays in one scan. An example of the fluorescence output resulting from such an experiment is shown in FIG. 15.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 5: Health Monitoring with an Array of the Invention

The in situ synthesized chemical library described herein can be used to detect and identify any disease for which a distinct antibody response develops. The same in situ synthesized chemical library can be used both in the discovery and application phases of biomarker development.

Figure 16:
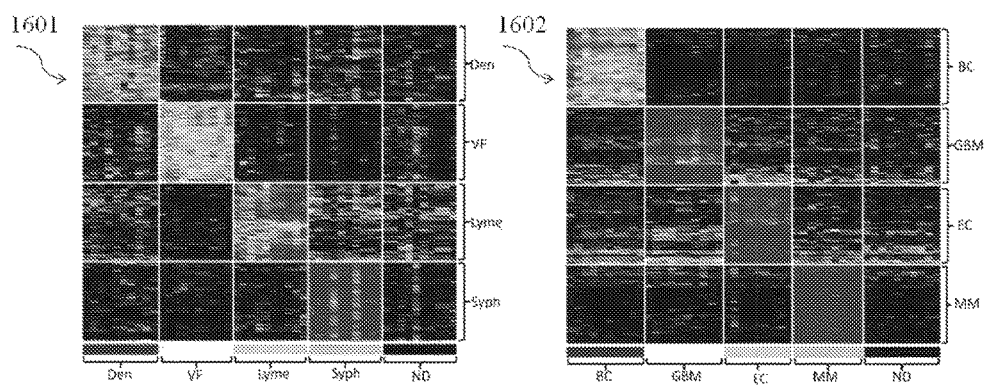
FIG. 16 is a heatmap indicating groupwise specificity of peptide signals.
Figure 17:
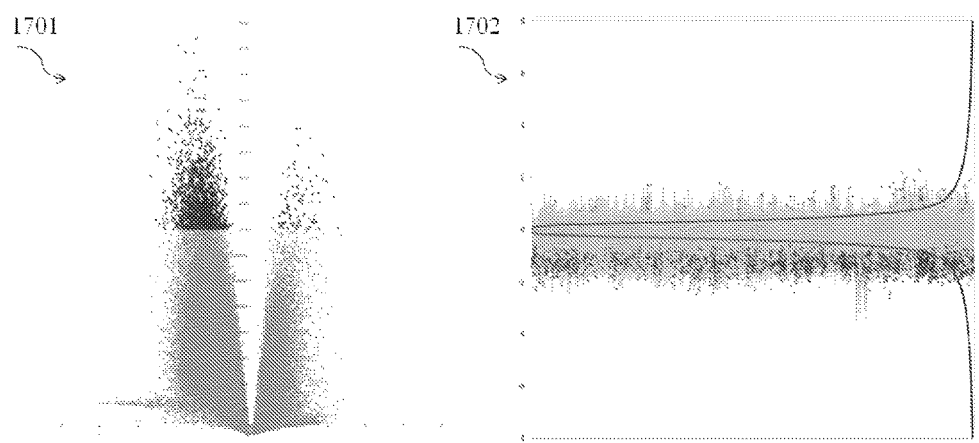
FIG. 17 is a graphical representation of a volcano plot and a power plot.

FIG. 16 shows the application of these arrays to the immunosignature detection and identification of infectious disease 1601 and cancer 1602 in sera. For these assays, there was no preprocessing of serum (whole blood can also be used, even dried on filter paper). Approximately 1 µl of serum was diluted 5000-fold in buffer and 200 µl of that was applied to an array, incubated for 1 hour and washed, followed by labeling with a secondary antibody for human IgG and the fluorescent binding intensity at each peptide was measured. 1601 is a heat map displaying the binding intensities of 800 peptides (y-axis) from the 330,000 peptide array that proved most informative in distinguishing four different infections (10 samples each of Dengue virus, Coccidioides, *Borrelia burgdorferi*, and *Treponema pallidum*) and from each other and non-infected individuals. The four different infectious diseases as well as sera from uninfected patients were simultaneously processed using Type I ANOVA and pattern matching using a cosine correlation method for feature selection that identifies peptides that gave the highest contrast signals between each disease and all other samples. The peptides shown in 1601 had p-values of p<10-27. A permuted t-test, based on scrambling the labels of the samples multiple times, gives no p-values less than 10-4). 1602 shows a heat map resulting from a similar analysis of four different cancers (breast cancer, glioblastoma multiforme, esophageal cancer and multiple myeloma). This figure demonstrates that the 330,000 peptide arrays can also simultaneously distinguish between different cancers. P-values of p<10-12 resulted from an ANOVA across the 4 different classes. FIG. 17 shows the average fold change (log base 2) between esophageal cancer and healthy controls for each peptide, along with an indication (black line) of the maximum fold-change that would be expected given the variation across the population within a disease for that peptide. There are 23,323 informative peptides on the array that contribute to distinguishing between these two diseases. FIG. 17 shows two different visualizations of the statistical power contained within the 330K arrays. 1701, is a volcano plot between eight esophageal cancer patients (negative $\log_2$ fold-change) and an equivalent number of healthy controls (positive $\log_2$ fold-change). Y-axis represents the $\log_{10}$ p-value, X-axis represents the $\log_2$ fold-change between EC (numerator) and ND (denominator). Red circles are peptides with $p<10^{-9}$. 1701 is a power plot demonstrating the calculated power (delta, black line) along the X-axis, the $\log_2$ fold-change values (blue bars, Y axis) from the comparison of eight EC and eight ND samples. The red circles indicate those peptides (X-axis) with $p<10^{-9}$.

Example 6: Optimization of Amino Acids of an Array of the Invention

In order to understand the impact on immunosignaturing performance by reducing peptide complexity, a number of different diseases and types of interactions were examined with regards to the contribution of individual amino acids. The data is listed in FIG. 18.

Experimental Details:

The experiments were performed on the version 1 10K peptide microarrays. Each peptide is a pre-synthesized 20 amino acids-long peptide with a GSG linker on the C-terminus, and 17 random-sequence residues subsequent. At least 50 patients from each class were tested multiple times against appropriate controls in order to ensure that informative peptides for each disease were consistent.

Non-Serum-Based Tests:

Further experiments were performed on 20 different monoclonal antibodies (listed as Antibodies), a broad number of sugars (Boltz et. al, 2009, "Peptide microarrays for Carbohydrate recognition", Analyst), proteins, and biotin. The peptides that discriminated these molecules were also ranked for the rate at which each residue appeared in discriminating peptides.

Results:

The number and type of residues that play a role in immunosignaturing different classes are seen in FIG. 18. Representation values of the total number of peptides that were compared for each test were obtained by dividing by 17. Decimals indicated that peptides that contained cysteine (5/10,000 were synthesized). 'Total' column is total number of residues accumulated for that class. In general, H, R, and K are over-represented for many classes of detection.

For breast cancer, it was found that H, R, K and W were substantially overrepresented in the peptide libraries. This indicated that eliminating these 4 residues would have a dramatic and negative impact on the ability to signature cancer. Experiments were also conducted for infectious diseases (viruses, fungi, healthy controls), chronic or aging-related diseases (Alzheimer's vs. controls), cancer (Breast cancer vs. controls) and ranked the frequency with which every amino acid appears in peptides that are informative for that disease diagnosis. FIG. 18 shows this ranking, and led to the removal of T and I as being least informative. I is generally present in the form of L, and T is similar in structure to S, neither of which presented sufficiently independent data suggesting they were needed for informative immunosignaturing.

Example 7: Evaluation of Tryptophan Elimination from Arrays

In order to understand the impact on immunosignaturing performance by eliminating certain amino acids, including tryptophan, the quality of immunosignature binding profiles were compared against S-Trp.

Figure 19:
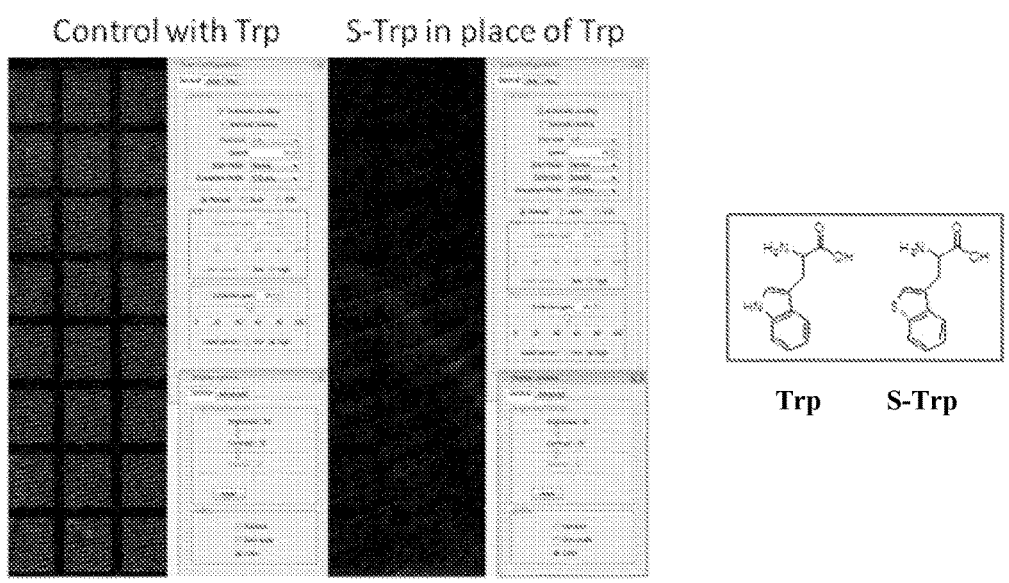
FIG. 19 illustrates the influence of tryptophan in immunosignature array analysis.

A monoclonal antibody against human TP53 which has a W in its recognition sequence was used to determine whether a chemically similar residue (S-Trp) could replace standard Trp. This antibody has exquisite specificity and did not recognize the Trp substitute under standard binding concentrations (5 nM final concentration of Ab). See FIG. 19. Scanning, incubation, temperature, were all kept standard.

EMBODIMENTS

The following non-limiting embodiments provide illustrative examples of the invention, but do not limit the scope of the invention.

Embodiment 1

An in situ synthesized chemical library, wherein said synthesis uses a minimum number of patterned steps to construct the library, comprising: a) determining a minimum number of patterned steps to synthesize the chemical library, wherein the minimum number of patterned steps is at least 33% of the number of patterned steps needed to construct an uncorrelated set of sequences in the chemical library and wherein the total number of patterned steps determines a degree of randomness of the chemical library; b) assigning an activated or inactivated designation to each feature; c) assigning a monomer to each feature that is designated as activated; and d) coupling the monomers on the substrate at each feature that is designated as activated; wherein the monomers are sequentially coupled for the minimum number of patterned steps of a).

Embodiment 2

The chemical library of Embodiment 1, wherein said synthesis is photolithography-based.

Embodiment 3

The chemical library of Embodiments 1 and 2, wherein the photolithography-based synthesis comprises a photomask pattern step.

Embodiment 4

The chemical library of any of Embodiments 1-3, wherein the photomasking step photomasks a feature of about 0.5 micron to about 200 microns in diameter and a center-to-center distance of about 1 micron to about 300 microns on center.

Embodiment 5

The chemical library of Embodiment 3, wherein the number of photomasks needed to construct the chemical library is about 33% to about 95% of the number of photomasks needed to construct a chemical library with an uncorrelated set of sequences.

Embodiment 6

The chemical library of Embodiment 3, wherein the number of photomasks needed to construct the chemical library is about 51% to about 75% of the number of photomasks needed to construct a chemical library with an uncorrelated set of sequences.

Embodiment 7

The chemical library of Embodiment 3, wherein the number of photomasks needed to construct the chemical library is about 51% to about 55% of the number of photomasks needed to construct a chemical library with an uncorrelated set of sequences.

Embodiment 8

The chemical library of Embodiment 3, wherein the determining the minimum number of patterned steps comprises determining the minimum number of steps needed to synthesize a unique set of sequences.

Embodiment 9

The chemical library of any one of Embodiments 1-8, wherein the library comprises at least 100,000 features on the substrate.

Embodiment 10

The chemical library of any one of Embodiments 1-8, wherein the library comprises at least 330,000 features on the substrate.

Embodiment 11

The chemical library of any one of Embodiments 1-8, wherein the library comprises at least 1,000,000 features on the substrate.

Embodiment 12

The chemical library of any one of Embodiments 1-8, wherein the library comprises at least 100,000,000 features on the substrate.

Embodiment 13

The chemical library of any one of Embodiments 1-12, wherein the substrate is selected from the group consisting of arrays, wafers, slides, and beads.

Embodiment 14

The chemical library of any one of Embodiments 1-13, wherein the synthesized chemical structures are peptides or nucleotides.

Embodiment 15

The chemical library of any one of Embodiments 1-14, wherein the peptides are about 5 amino acids to about 25 amino acids in length.

Embodiment 16

The chemical library of any one of Embodiments 14 and 15, wherein the amino acids C, I, T, and M, and optionally Q and E, are not included in the amino acids available for peptide synthesis.

Embodiment 17

The chemical library of any one of Embodiments 14, 15 and 16, wherein the peptide lengths are not uniform between the features.

Embodiment 18

The chemical library of any one of Embodiments 3-16, wherein each feature is randomly assigned an activated or inactivated designation.

Embodiment 19

A method of in situ synthesizing a chemical library on a substrate, wherein the number of patterning steps needed to construct the library are minimized, the method comprising: a) determining a minimum number of patterned steps to synthesize the chemical library, wherein the minimum number of patterned steps is at least 33% of the number of patterned steps needed to construct an uncorrelated set of sequences in the chemical library and wherein the total number of patterned steps determines a degree of randomness of the chemical library; b) assigning an activated or inactivated designation to each feature; c) assigning a monomer to each feature that is designated as activated; and d) coupling the monomers on the substrate at each feature that is designated as activated; wherein the monomers are sequentially coupled for the minimum number of patterned steps of a).

Embodiment 18

The method of Embodiment 17, wherein said synthesis is photolithography-based.

Embodiment 19

The method of any one of Embodiments 17 and 18, wherein the photolithography-based synthesis comprises a photomask patterned step.

Embodiment 20

The method of any of Embodiments 17-19, wherein the photomask step photomasks a feature of about 0.5 micron to about 200 microns in diameter and a center-to-center distance of about 1 micron to about 300 microns on center.

Embodiment 21

The method of Embodiment 19, wherein the number of photomasks needed to construct the chemical library is about 33% to about 95% of the number of photomasks needed to construct a chemical library with an uncorrelated set of sequences.

Embodiment 22

The method of Embodiment 19, wherein the number of photomasks needed to construct the chemical library is about 51% to about 75% of the number of photomasks needed to construct a chemical library with an uncorrelated set of sequences.

Embodiment 23

The method of Embodiment 19, wherein the number of photomasks needed to construct the chemical library is about 51% to about 55% of the number of photomasks needed to construct a chemical library with an uncorrelated set of sequences.

Embodiment 24

The method of any of Embodiments 17-23, wherein the determining the minimum number of patterned steps comprises determining the minimum number of steps needed to synthesize a unique set of sequences.

Embodiment 25

The method of any one of Embodiments 17-24, wherein the library comprises at least 100,000 features on the substrate.

Embodiment 26

The method of any one of Embodiments 17-24, wherein the library comprises at least 330,000 features on the substrate.

Embodiment 27

The method of any one of Embodiments 17-24, wherein the library comprises at least 1,000,000 features on the substrate.

Embodiment 28

The method of any one of Embodiments 17-24, wherein the library comprises at least 100,000,000 features on the substrate.

Embodiment 29

The method of any one of Embodiments 17-28, wherein the substrate is selected from the group consisting of arrays, wafers, slides and beads.

Embodiment 30

The method of any one of Embodiments 17-29, wherein the synthesized chemical structures are peptides or nucleotides.

Embodiment 31

The method of any one of Embodiments 17-30, wherein the peptides are about 5 amino acids to about 25 amino acids in length.

Embodiment 32

The method of any one of Embodiments 30 and 31, wherein the amino acids C, I, T, and M, and optionally Q and E, are not included in the amino acids available for peptide synthesis.

What is claimed is:

1. An in situ synthesized pseudo random peptide library for use in an immunosignature assay, wherein synthesis of the pseudo random peptide library uses a minimum number of patterned steps to construct the pseudo random peptide library on a substrate, wherein the minimum number of patterned steps (M) is less than the product of the number of different monomer units (R) and the length of the peptide (N) according to $$M < R \times N,$$

comprising:
a) determining the minimum number of patterned steps (M), wherein the minimum number of patterned steps (M) is at least 33% of the number of patterned steps needed to construct an uncorrelated set of sequences in the pseudo random peptide library, wherein the peptide library is disease agnostic;
b) assigning an activated or inactivated designation to each feature of a patterned step;
c) assigning a monomer to each feature that is designated as activated; and
d) coupling the monomers at each feature on the substrate that is designated as activated; wherein the monomers are sequentially coupled for the minimum number of patterned steps of (a), thereby providing a pseudo-random array for use in the immunosignature assay.

2. The pseudo random peptide library of claim 1, wherein said synthesis is photolithography-based.

3. The pseudo random peptide library of claim 2, wherein the photolithography-based synthesis comprises a photomask pattern step.

4. The pseudo random peptide library of claim 3, wherein the photomasking step photomasks a feature of about 0.5 micron to about 200 microns in diameter and a center-to-center distance of about 1 micron to about 300 microns on center.

5. The pseudo random peptide library of claim 3, wherein the number of photomasks needed to construct the peptide library is about 33% to about 95% of the number of photomasks needed to construct a peptide library with an uncorrelated set of sequences.

6. The pseudo random peptide library of claim 3, wherein the number of photomasks needed to construct the peptide library is about 51% to about 75% of the number of photomasks needed to construct a peptide library with an uncorrelated set of sequences.

7. The pseudo random peptide library of claim 3, wherein the number of photomasks needed to construct the peptide library is about 51% to about 55% of the number of photomasks needed to construct a peptide library with an uncorrelated set of sequences.

8. The pseudo random peptide library of claim 3, wherein each feature on each photomask is randomly assigned an activated or inactivated designation.

9. The pseudo random peptide library of claim 1, wherein the library comprises at least 10,000 features on the substrate.

10. The pseudo random peptide library of claim 1, wherein the library comprises at least 100,000 features on the substrate.

11. The pseudo random peptide library of claim 1, wherein the library comprises at least 330,000 features on the substrate.

12. The pseudo random peptide library of claim 1, wherein the library comprises at least 1,000,000 features on the substrate.

13. The pseudo random peptide library of claim 1, wherein the substrate is selected from the group consisting of arrays, wafers, slides, and beads.

14. The pseudo random peptide library of claim 1, wherein the peptides are about 5 amino acids to about 25 amino acids in length.

15. The pseudo random peptide library of claim 14, wherein the peptide lengths are not uniform between features.

16. The pseudo random peptide library of claim 1, wherein amino acids C, I, T, and M, and optionally Q and E, are not included as amino acids available during peptide synthesis.

17. The pseudo random peptide library of claim 1, wherein the activated designation is clear.

18. The pseudo random peptide library of claim 1, wherein the inactivated designation is opaque.

19. The pseudo random peptide library of claim 1, wherein the coupling of the monomers at each feature forms a linear or a branched structure.

* * * * *